(12) United States Patent
Fachin et al.

(10) Patent No.: US 11,912,978 B2
(45) Date of Patent: Feb. 27, 2024

(54) FLOW-THROUGH PARAMAGNETIC PARTICLE-BASED CELL SEPARATION AND PARAMAGNETIC PARTICLE REMOVAL

(71) Applicants: Novartis AG, Basel (CH); The Trustees of the University of Pennsylvania, Philadelphia, PA (US)

(72) Inventors: Fabio Fachin, Cambridge, MA (US); Rodney Rietze, Cambridge, MA (US); Michael R. Greene, Cambridge, MA (US); Lan Cao, East Hanover, NJ (US)

(73) Assignees: Novartis AG, Basel (CH); The Trustees of the University of Pennsylvania

( * ) Notice: Subject to any disclaimer, the term of this patent is extended or adjusted under 35 U.S.C. 154(b) by 207 days.

(21) Appl. No.: 17/503,186

(22) Filed: Oct. 15, 2021

(65) Prior Publication Data

US 2022/0135931 A1 May 5, 2022

Related U.S. Application Data

(60) Continuation of application No. 16/739,573, filed on Jan. 10, 2020, now Pat. No. 11,162,065, which is a
(Continued)

(51) Int. Cl.
*C12M 1/00* (2006.01)
*B03C 1/01* (2006.01)
(Continued)

(52) U.S. Cl.
CPC ............. *C12M 47/04* (2013.01); *B03C 1/01* (2013.01); *B03C 1/0332* (2013.01); *B03C 1/288* (2013.01);
(Continued)

(58) Field of Classification Search
CPC .. A61K 2039/505; B03C 1/01; B03C 1/0332; B03C 1/288; B03C 1/30; B03C 2201/26;
(Continued)

(56) References Cited

U.S. PATENT DOCUMENTS

| 4,219,411 A | 8/1980 | Molday et al. |
| 4,855,045 A * | 8/1989 | Reed ...................... B03C 1/288 |
| | | 435/178 |

(Continued)

FOREIGN PATENT DOCUMENTS

| CN | 1630526 A | 6/2005 |
| CN | 101019026 A | 8/2007 |

(Continued)

OTHER PUBLICATIONS

Japanese Final Notification of Reasons for Refusal dated Mar. 10, 2023, for Application No. 2021-091480, 7 pages.
(Continued)

*Primary Examiner* — Claire A Norris
(74) *Attorney, Agent, or Firm* — Frost Brown Todd LLP

(57) ABSTRACT

The present disclosure relates to systems and methods for flow-through separation of paramagnetic particle-bound cells in a cell suspension containing both bound and unbound cells as well as systems and methods for removing paramagnetic particles from paramagnetic particle-bound cells or from a cell suspension with unbound cells. It further relates to a flow-through magnetic separation/debeading module and a flow-through spinning membrane debeading module.

17 Claims, 19 Drawing Sheets

Related U.S. Application Data division of application No. 15/172,415, filed on Jun. 3, 2016, now abandoned.

(60) Provisional application No. 62/173,702, filed on Jun. 10, 2015, provisional application No. 62/171,787, filed on Jun. 5, 2015.

(51) Int. Cl.

| | | |
|---|---|---|
| *B03C 1/033* | (2006.01) | |
| *B03C 1/28* | (2006.01) | |
| *B03C 1/30* | (2006.01) | |
| *C07K 16/28* | (2006.01) | |
| *C12M 1/12* | (2006.01) | |
| *C12N 13/00* | (2006.01) | |
| *A61K 39/00* | (2006.01) | |

(52) U.S. Cl.
CPC ............ *B03C 1/30* (2013.01); *C07K 16/2803* (2013.01); *C07K 16/2809* (2013.01); *C07K 16/2818* (2013.01); *C12M 25/02* (2013.01); *C12N 13/00* (2013.01); *A61K 2039/505* (2013.01)

(58) Field of Classification Search
CPC ............ C07K 16/2803; C07K 16/2809; C07K 16/2818; C12M 25/02; C12M 47/04; C12N 13/00
USPC ..................................................... 435/173.9
See application file for complete search history.

(56) References Cited

U.S. PATENT DOCUMENTS

| | | | |
|---|---|---|---|
| 5,194,145 A | | 3/1993 | Schoendorfer |
| 5,536,475 A | * | 7/1996 | Moubayed ....... G01N 33/56966 |
| | | | 209/225 |
| 11,162,065 B2 | | 11/2021 | Fachin et al. |
| 2001/0035377 A1 | * | 11/2001 | Johnson ................ A61M 1/262 |
| | | | 210/645 |
| 2005/0274650 A1 | | 12/2005 | Frazier et al. |
| 2007/0196820 A1 | | 8/2007 | Kapur et al. |
| 2010/0311559 A1 | | 12/2010 | Miltenyi et al. |
| 2011/0003380 A1 | | 1/2011 | Miltenyi et al. |
| 2011/0059468 A1 | | 3/2011 | Earhart et al. |
| 2011/0127222 A1 | | 6/2011 | Chang-yen et al. |
| 2011/0294139 A1 | | 12/2011 | Takeda |
| 2012/0080360 A1 | | 4/2012 | Stone et al. |
| 2012/0135494 A1 | | 5/2012 | Murthy et al. |
| 2012/0244529 A1 | * | 9/2012 | Fuchs .................... B01L 3/5027 |
| | | | 435/7.1 |
| 2012/0264200 A1 | | 10/2012 | Hedrick et al. |
| 2013/0341291 A1 | | 12/2013 | Wegener et al. |
| 2014/0021105 A1 | | 1/2014 | Lee et al. |
| 2015/0101994 A1 | | 4/2015 | Najdeni |
| 2016/0244714 A1 | | 8/2016 | Spuhler et al. |
| 2016/0355777 A1 | | 12/2016 | Fachin et al. |

FOREIGN PATENT DOCUMENTS

| | | |
|---|---|---|
| CN | 101078028 A | 11/2007 |
| CN | 101305087 A | 11/2008 |
| CN | 103415329 A | 11/2013 |
| EP | 1572071 A2 | 9/2005 |
| EP | 1934326 A2 | 6/2008 |
| EP | 2227271 A2 | 9/2010 |
| EP | 2579988 A2 | 4/2013 |
| EP | 2683455 A1 | 1/2014 |
| EP | 2859905 A1 | 4/2015 |
| EP | 3058316 A1 | 8/2016 |
| JP | 2004-154151 A | 6/2004 |
| JP | 2005-519883 A | 7/2005 |
| JP | 2007-143524 A | 6/2007 |
| JP | 2009-511001 A | 3/2009 |
| JP | 2011-505890 A | 3/2011 |
| JP | 2014-509854 A | 4/2014 |
| JP | 2018-134465 A | 8/2018 |
| KR | 10-2010-0029272 A | 3/2010 |
| TW | 201121655 A | 7/2011 |
| WO | WO-9626782 A1 * | 9/1996 .......... A61M 1/3603 |
| WO | 2003/053346 A2 | 7/2003 |
| WO | WO 2006/001196 A1 | 1/2006 |
| WO | 2007/035498 A2 | 3/2007 |
| WO | 2008/048616 A2 | 4/2008 |
| WO | 2009/072003 A2 | 6/2009 |
| WO | 2012/004363 A2 | 1/2012 |
| WO | 2012/079000 A1 | 6/2012 |
| WO | 2012/125470 A1 | 9/2012 |
| WO | 2015/034428 A1 | 3/2015 |
| WO | 2015/058206 A1 | 4/2015 |
| WO | 2016/207911 A2 | 12/2016 |
| WO | WO 2015/005299 A1 | 3/2017 |

OTHER PUBLICATIONS

Taiwan Office Action and Search Report dated Feb. 3, 2023, for Application No. 110135897, 3 pages.
Karabacak et al., "Microfluidic, Marker-Free Isolation of Circulating Tumor Cells from Blood Samples", Nature protocols, vol. 9, No. 3, 2014, pp. 694-710.
Nexell Therapeutics Inc., "Hematopoietic Stem Cell Concentration System", Summary of Safety and Effectiveness, Isolex® 300 Magnetic Cell Selection System and Isolex® 300i Magnetic Cell Selection System, Jul. 2, 1999, 32 pages.
Non-Final Office Action received for U.S. Appl. No. 16/739,573, dated Feb. 5, 2021, 2021, 8 pages.
Notice of Allowance received for U.S. Appl. No. 16/739,573, dated Jul. 27, 2021, 7 pages.
Ozkumur et al., "Inertial focusing for tumor antigen-dependent and -independent sorting of rare circulating tumor cells", Science translational medicine, vol. 5, No. 179, 2013, 13 pages.

* cited by examiner

FLOW-THROUGH PARAMAGNETIC PARTICLE-BASED CELL SEPARATION AND PARAMAGNETIC PARTICLE REMOVAL

PRIORITY CLAIM

The present application is a continuation of U.S. patent application Ser. No. 16/739,573, filed Jan. 10, 2020, which is a divisional application of U.S. patent application Ser. No. 15/172,415 filed Jun. 3, 2016, which claims priority under 35 U.S.C. § 119 to U.S. Provisional Patent Application Ser. No. 62/171,787 filed Jun. 5, 2015 and U.S. Provisional Patent Application Ser. No. 62/173,702 filed Jun. 10, 2015, the contents of which are hereby incorporated by reference in their entirety.

TECHNICAL FIELD

The present disclosure relates to systems and methods for flow-through separation of paramagnetic particle-bound cells in a cell suspension containing both bound and unbound cells as well as systems and methods for removing paramagnetic particles from paramagnetic particle-bound cells or from a cell suspension with unbound cells.

BACKGROUND

Particles may be present in the external environment of cells for any number of reasons. For example, particles are often coated with a growth-inducer, which causes responsive cells in a mixed-cell or single-cell culture to grow and divide. Particles are also often coated with a binding agent, which attaches to a particular type of cell, allowing it to be separated from other types of cells in the same mixed-cell suspension. This separation based on cell type allows desirable cells to be separated from undesirable cells.

Although particles are useful for their intended function, the presence of particles in a cell product may later be detrimental. For instance, the particles themselves may pose a risk of harm to a patient receiving the cell product for cell therapy. In other cases, the particles may hamper further growth and division of the cells, or they may need to be removed so that growth and division slow or to allow the cells to differentiate.

Various types of particles may be removed from the cell product in any of a number of ways, but paramagnetic particles are often used because their attraction to a magnet allows both separation of paramagnetic particle-bound cells from unbound cells and paramagnetic particle removal from paramagnetic particle-bound cells.

Current systems and methods using paramagnetic particles for cell separation place a cell suspension containing paramagnetic particle-bound cells in a suspension fluid in a chamber, then position a magnet near a chamber wall. Free paramagnetic particles and those bound to cells are attracted to the magnet and, therefore, are held in position on the inner wall of the chamber adjacent to the magnet. The remaining suspension fluid, containing any unbound cells, is removed. Then the magnet is moved away from the chamber wall, releasing the paramagnetic particles and any paramagnetic particle-bound cells.

Such a system and method may be used for either positive or negative selection of paramagnetic particle-bound cells, but it has many drawbacks in either instance. One drawback is that paramagnetic particles and paramagnetic particle-bound cells may enter the unbound cell product via the unbound cell output fraction because there is not sufficient surface area to accommodate them on the chamber wall, because other cells impede them reaching the chamber wall, because they are part of a cell clump that is too large to remain magnetically attached to the chamber wall, or for other reasons. If the unbound cells are to be used clinically, this contamination is a health hazard. If the unbound cells are waste, then desirable cells are lost.

Another drawback is that unbound cells may be trapped in layers of paramagnetic particle-bound cells, again resulting in cells being in the wrong cell output fraction, which may lead to waste or unwanted contamination.

Layering of cells on the chamber wall presents yet another drawback in that this layering may cause the cells to clump, interfering with later processing or use, or their access to nutrients. Layering may even cause some cells to be crushed, either destroying desirable cells or introducing cell lysis contaminants into the cell suspension.

Similar systems and methods are used to remove paramagnetic particles from cells in a process called debeading. In debeading, a cell suspension is placed in a chamber and a magnet positioned near the chamber wall to attract paramagnetic particles Such a system and method also has a number of drawbacks including the possible inclusion of cells with paramagnetic particles in the unbound cell fraction and ultimately the unbound cell product, usually because they simply were not attracted to the wall. For instance, because a magnetic field is inversely proportional to the square of the distance from the magnet, it falls off rather quickly as one moves away from the chamber wall. If too large of a chamber or too weak of a magnet is used, the chances of paramagnetic particle-bound cells ending up in the unbound cell product is higher.

Systems and methods able to separate or debead paramagnetic particle-bound cells while addressing one or more of these drawbacks are needed.

SUMMARY

In one aspect, the present disclosure provides a cell processing system including at least one cell suspension module; at least one buffer module; at least one flow-through magnetic separation/debeading module; at least one non-magnetic output module; and at least one magnetic output module.

In some variations of this system, it may include at least one return loop returning upstream of at least one flow-through magnetic separation/debeading module; at least two flow-through magnetic separation/debeading modules in parallel; at least two flow-through magnetic separation/debeading modules in series; at least one additional module, or any combinations thereof. The at least one additional module may include at least one spinning membrane debeading module; at least two spinning membrane debeading modules in parallel; or at least two spinning membrane debeading modules in series. Any of the spinning membrane debeading modules may include at least one magnet adjacent or proximate to a cylindrical side-wall.

In a more specific variation, the flow-through magnetic separation/debeading module includes a chamber defined by walls and having an x-direction, a y-direction, and a z-direction; an inlet and an outlet arranged on opposite ends of the chamber in the y-direction; and at least two magnets adjacent or proximate a wall of the chamber and arranged to establish a zero gradient line within the chamber between the inlet and the outlet.

In another more specific variation, which may stand alone or be combined with the first more specific variation, the spinning membrane debeading module includes a debeading chamber define partially by a cylindrical side-wall; a porous spinning membrane having an interior and oriented co-axially with the cylindrical side-wall; a sample inlet; a waste output module connected to the interior of the spinning membrane; and a cell output module connected to the debeading chamber.

In another aspect, the disclosure provides a flow-through magnetic separation/debeading module including a chamber defined by walls and having an x-direction, a y-direction, and a z-direction; an inlet and an outlet arranged on opposite ends of the chamber in the y-direction; and at least two magnets adjacent or proximate a wall of the chamber and arranged to establish a zero gradient line within the chamber between the inlet and the outlet.

In some variations of this module, it includes it least two inlets and at least two outlets; at least three magnets adjacent or proximate a wall of the chamber and arranged to establish at least two zero gradient lines within the chamber between the inlet and the outlet; at least four magnets arranged in two arrays on opposite sides of the chamber in the z-direction; at least four magnets arranged in two arrays on opposite sides of the chamber in the z-direction and cross-oriented in the x-y plane from near one inlet to near one outlet on the opposite side of the chamber in the z-direction; a sub-membrane injection ports adjacent a wall of the chamber also adjacent at least two magnets and a membrane adjacent the sub-membrane; or any combinations thereof.

In another aspect, the disclosure provides a spinning membrane debeading module including a debeading chamber define partially by a cylindrical side-wall; a porous spinning membrane having an interior and oriented co-axially with the cylindrical side-wall; a sample inlet; a waste output module connected to the interior of the spinning membrane; a cell output module connected to the debeading chamber; and at least one magnet adjacent or proximate to the cylindrical side-wall.

In some variations of this module, it may include a reagent module, have a pore size greater than that of a particle to be debeaded and less than that of a cell to be debeaded, or both.

In yet another aspect, the disclosure provides a method of flow-through cell processing by flowing a cell suspension comprising paramagnetic particle-bound cells through a flow-through magnetic separation/debeading module to produce an unbound cell product. The paramagnetic particle-bound cells continue to move in the flow-through magnetic separation/debeading module through the flowing step. The flow-through magnetic separation/debeading module includes a flow chamber defined by walls through which the cell suspension flows and at least two magnets arranged adjacent or proximate at least one wall.

In some variations of this method, the cell suspension is flowed laminarly through the flow-through magnetic separation/debeading module; the cell suspension further includes unbound cells and flowing the cell suspension through the flow-through magnetic separation/debeading module separates the paramagnetic particle-bound cells and the unbound cells; the cell suspension further includes free paramagnetic particles and flowing the cell suspension through the flow-through magnetic separation/debeading module separates the free paramagnetic particles and the unbound cells, or any combinations thereof.

The method may also include flowing the separated unbound cells through the flow-through magnetic separation/debeading module a second or subsequent time using a return loop; flowing the separated paramagnetic particle-bound cells through the flow-through magnetic separation/debeading module a second or subsequent time using a return loop; debeading the paramagnetic particle-bound cells in the flow-through magnetic separation/debeading module during the second or subsequent time to produce paramagnetic particles and debeaded, unbound cells; flowing the produced paramagnetic particles and debeaded, unbound cells through the flow-through magnetic separation/debeading module a third or subsequent time to separate the paramagnetic particles and the debeaded, unbound cells, or any combinations thereof.

In another variation, combinable with all others, the magnets are oriented to establish one zero gradient line that crosses the direction of flow, such that paramagnetic-particle bound cells are pulled to the zero gradient line in one direction only, but are not affected by magnetic forces from the magnets in two other directions.

In another variation, combinable with all others, the chamber further includes a magnetic inlet through which any paramagnetic particles enter the flow chamber; a non-magnetic inlet; a magnetic outlet opposite the non-magnetic inlet; and a non-magnetic outlet opposite the magnetic inlet, wherein the zero gradient line directs all paramagnetic particles and any paramagnetic particle-bound cells to the magnetic outlet.

The cell suspension may further include unbound cells and the non-magnetic inlet may be larger than the magnetic inlet while the non-magnetic outlet is larger than magnetic outlet, so that fluid flowing from the non-magnetic inlet crosses over to the non-magnetic outlet, preventing any unbound cells from flowing into the magnetic outlet.

Alternatively, the cell suspension may further include unbound cells, and the non-magnetic inlet and magnetic inlet may be substantially the same size or the non-magnetic outlet and magnetic outlet may be substantially the same size, or both, and the respective flow rates of the fluid entering the inlets, the respective flow rates of the fluid exiting the outlets, or both may be adjusted such that fluid flowing from the non-magnetic inlet crosses over to the non-magnetic outlet, preventing any unbound cells from flowing into the magnetic outlet.

In another variation, combinable with all others, the method may include flowing the paramagnetic particle-bound cells through a spinning membrane debeading module to produce the unbound cell product. The spinning membrane debeading module may include a cylindrical debeading chamber through which the paramagnetic particle-bound cells flow, the chamber defined in part by a cylindrical side-wall and containing a co-axial spinning membrane; and at least one magnet arranged adjacent or proximate the cylindrical side-wall to establish at least one zero gradient line within the cylindrical debeading chamber.

In another aspect, the disclosure provides a method of manufacturing a cell therapy composition by contacting a cell population with paramagnetic particles coated with one or more agents which assist in expanding one or more cell types within the cell population; introducing nucleic acid into cells within the cell population; expanding cells within the cell population; debeading the cell population according to any of the above systems or methods or any other system or method described herein; and formulating the cell population for cell therapy.

In some variations, the one or more agents which assist in expanding one or more cell types may include anti-CD3 antibody or antigen binding fragment thereof, anti-CD28 antibody or antigen binding fragment thereof, and combinations thereof the nucleic acid may be introduced by lentivirus or mRNA transduction; the cell therapy may be a chimeric antigen receptor T cell therapy; the cell therapy is an anti-CD19 chimeric antigen receptor T cell therapy; or any combinations thereof.

BRIEF DESCRIPTION OF THE DRAWINGS

A more complete understanding of the present disclosure and advantages thereof may be acquired by referring to the following description taken in conjunction with the accompanying drawings, which are not to scale and in which like numerals refer to like features.

DETAILED DESCRIPTION

The present disclosure relates to systems and methods for flow-through separation, debeading, paramagnetic particle separation, or any combination thereof of paramagnetic particle-bound cells or unbound cells in the presence of paramagnetic particles, in a cell suspension. The systems and methods use a flow-through magnetic separation/debeading module, a spinning membrane debeading module, or both. Although the systems and methods described herein may be used to remove paramagnetic particles from any type of cell, they are particularly well-adapted for use in removing paramagnetic particles from cells to be used in cell therapy. In addition, although some portions of the description focus on positive selection of paramagnetic particle-bound cells, as debeading is typically only performed during positive selection methods, the systems and methods may also be used for negative selection. When used for negative selection, typically any debeading modules and steps will be eliminated.

Separation and Debeading Systems and Modules

Figure 1A:
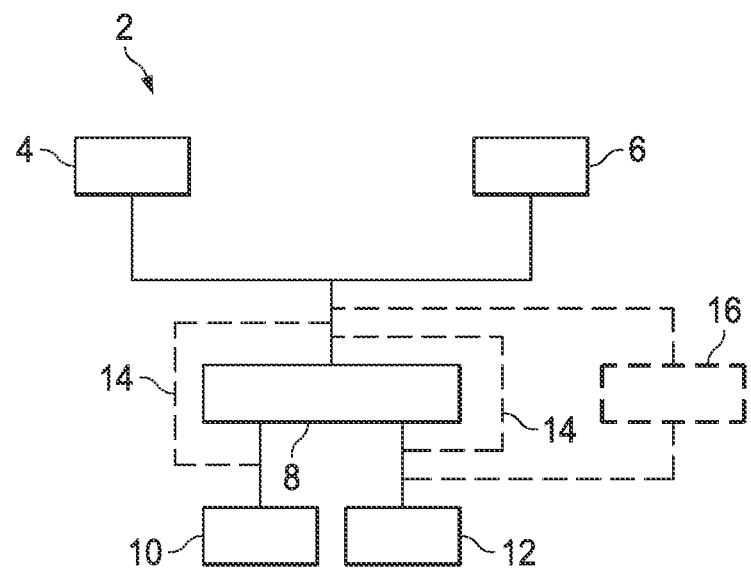
FIG. 1A is a schematic diagram of a cell processing system with a flow-through magnetic separation/debeading module.

FIG. 1A is a schematic diagram of a cell processing system 2 for flow-through separation, debeading, paramagnetic particle separation, or any combination thereof of paramagnetic particle-bound cells in a cell suspension. System 2 includes cell suspension module 4, buffer module 6, flow-through magnetic separation/debeading module 8, non-magnetic output module 10, and magnetic output module 12. System 2 may optionally also include at least one additional module 16, at least one return loop 14, or both.

System 2 additionally may include fluid conduits, such as tubes or hoses, connectors, valves, switches, clamps, weld sites, housings, motors, pumps, other mechanical mechanisms, circuitry, monitoring devices, and control devices. System 2 may further include a computer programmed to control system 2 or any component thereof to perform a flow-through separation process, a flow-through debeading process, a flow-through paramagnetic particle separation process, or any combination thereof.

System 2 may have a static configuration, or it may have an adaptable configuration. One adaptable configuration may allow the exchange of modules or the insertion of additional modules. Another adaptable configuration may have an unchangeable set of modules, but may allow changes in fluid routing to at least one of the modules. Other adaptable configurations may allow both exchange and addition of modules as well as changes in fluid routing. Components of system 2 may facilitate the adaptable configuration. For instance, a programmed computer in system 2 may detect or use information regarding which modules are present or it may control fluid routing. In addition, system 2 may be have housings or fluid conduits with accompanying connectors, valves, clamps, or switches that allow removal or insertion of different modules in the same location. Modules or other components may contain identification elements, such as bar codes or radio frequency identification (RFID) chips, to allow their presence or absence to be automatically detected. Modules or other components may also contain one or more indication elements, which may ensure compliance with good manufacturing practices and other safety regulations. For instance, temperature sensitive indication elements may indicate that a module or other component has been heat sterilized or not subjected to a temperature that may compromise its integrity or effectiveness. Indication elements may also clearly identify used modules or other components. Indication elements may also be automatically detected by system 2, helping to minimize human error.

Components of system 2 not needed for a particular process may be absent, unconnected, or closed. For instance, a single output module may be present rather than a separate non-magnetic output module 10 and magnetic output module 12, as shown in FIG. 1H. In addition, also as illustrated in FIG. 1H, the components of system 2 may have fluid conduits with different routes and connections than as shown in FIG. 1A, depending on the configuration of valves, clamps, weld sites, switches, and connectors.

Cell suspension module 4 contains cells to be separated or debeaded suspended in a suspension fluid. If the cells are to be separated, then typically the cell suspension contains both paramagnetic particle-bound cells and unbound cells. The paramagnetic particle-bound cells may be the desirable cells, in which case positive selection for paramagnetic cells will occur in system 2, or the paramagnetic particle-bound cells may be undesirable, in which case negative selection for the paramagnetic particle-bound cells will occur.

If the cells are to be debeaded, or if paramagnetic particles are to be separated from the cells, then the paramagnetic particle-bound cells are desirable cells. They may have previously been separated from undesirable cells using system 2 or another system. In instances where the presence of undesirable cells is not problematic or where there are no undesirable cells to separate, the cells to be debeaded may not have previously undergone a separation process.

The cells may be obtained directly from a biological sample, such as blood, or from a cell culture.

The suspension fluid may be any fluid able to support viability of the cells throughout the separation, debeading, or particle removal process. For instance, it may be a culture medium, a freezing agent, such as a DMSO-containing fluid, another fluid with a set or controlled pH, or another fluid with nutrients. It may also be a buffer, which may be the same as or different from the buffer in buffer module 6. The suspension fluid may have a different viscosity than the buffer. It may also have a different viscosity than the medium in which the cells enter system 2, which may be very dense, such as high density Ficoll.

The buffer in buffer module 6 may be any fluid that may be combined with the suspension fluid while allowing the suspension fluid to continue to support viability of the cells. For instance, the buffer may have a set or controlled pH. The buffer may include one or more cell-compatible salts. Although buffer is provided separately in buffer module 6, once the buffer mixes with the cell suspension, it is considered to be part of the suspension fluid.

The suspension fluid or buffer may contain antimicrobial agents, but typically will not if the cells will later be provided to a patient unless system 2 removes these agents, such as via a spinning membrane debeading module or another module, or unless they are removed later by an additional process, module, or system.

The paramagnetic particles may be formed from any paramagnetic and/or magnetizable material, such as a metal or metal alloy. Typically the paramagnetic material is not toxic to the cells or to any patient who will later receive the cells, or it is coated to avoid toxicity. The paramagnetic material may be selected to achieve a high magnetic saturation flux (ms). In general, which paramagnetic materials are suitable is influenced by the magnets used in system 2 and the configuration of modules using the magnets, as these elements influence driving the paramagnetic material to magnetic saturation.

The paramagnetic particles may be coated with a binding agent, such as a growth agent, a receptor or ligand, an antigen, an antibody, or any binding fragments or chimeric variants thereof, such as a chimeric antigen receptor ligand. The binding agents may be reversible in some instances, allowing detachment of the paramagnetic particles spontaneously or using a particular chemical agent. The binding agents may also include a photo-cleavable linker, in which case system 2 may include a light source, particularly a high power light source, as a module or as part of another module to allow photo-cleavage of the linker and separation of the cell and paramagnetic particle. In some instances, the coating may interact with the cells. In other instances, the coating may interact with at least one unwanted constituent of the cell suspension that is to be removed. The unwanted constituent may be active or inactive and may have previously served a useful function with respect to the cells or the cell suspension fluid. Example unwanted constituents include antibodies, growth factors, other proteins, and polymers.

Different types of paramagnetic particles, such as particles with different binding agents or formed from different magnetic materials may be present in some cell suspensions, allowing for complex separations or iterative removal of binding agents. Additional, non-paramagnetic particles, which may also be coated with any binding agent, may also be bound to cells.

Other particles that are not paramagnetic may also be present in the cell suspension and may be coated with anything used to coat the paramagnetic particles.

Modules may be formed from or lined with any biologically compatible material such as cell storage bags. Fluid conduits and any other component of system 2 that contacts the cell suspension or buffer may also be formed from or lined with any biologically compatible material.

Components of system 2 that will contact the cell suspension or buffer may be sterile prior to contact with the cell suspension.

Components of system 2 may be disposable. Components that contact the cell suspension, in particular, may be disposable to avoid contamination and sterility concerns.

Figure 2A:
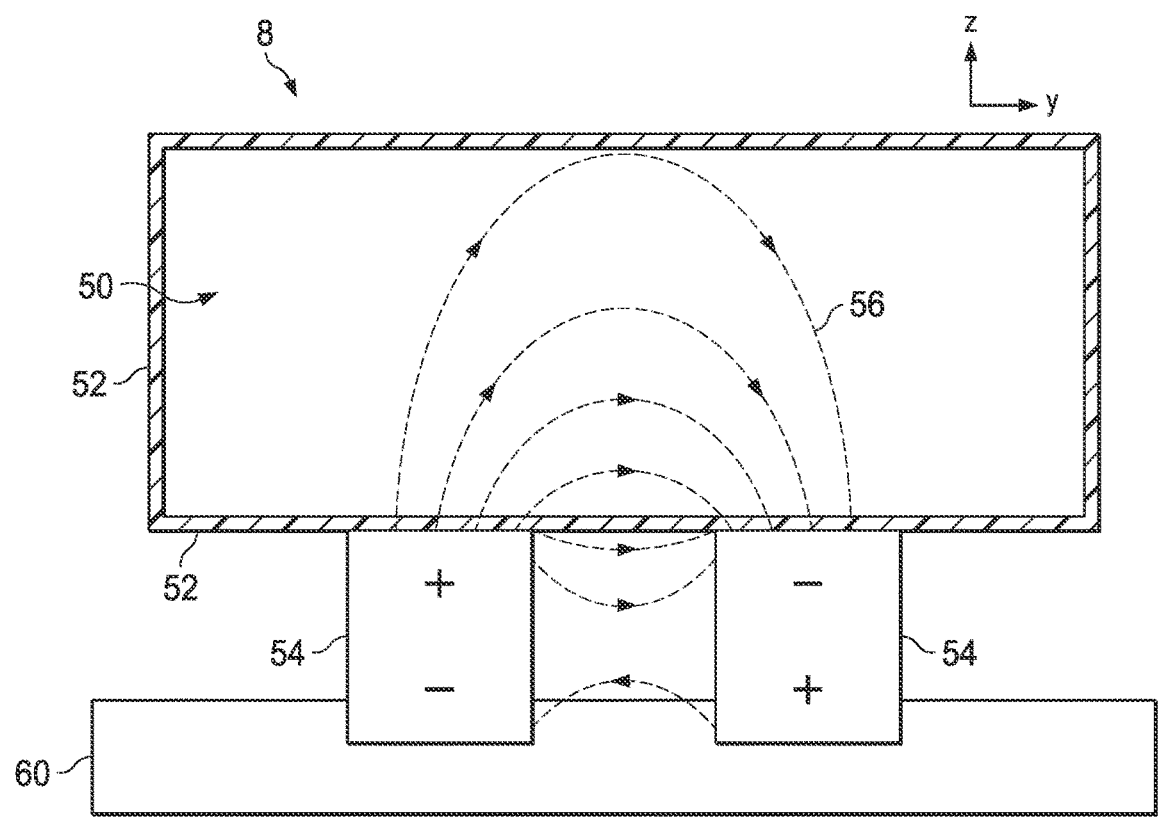
FIG. 2A is a transverse cross-sectional schematic diagram of a flow-through magnetic separation/debeading module in an x-oriented magnet configuration.
Figure 2B:
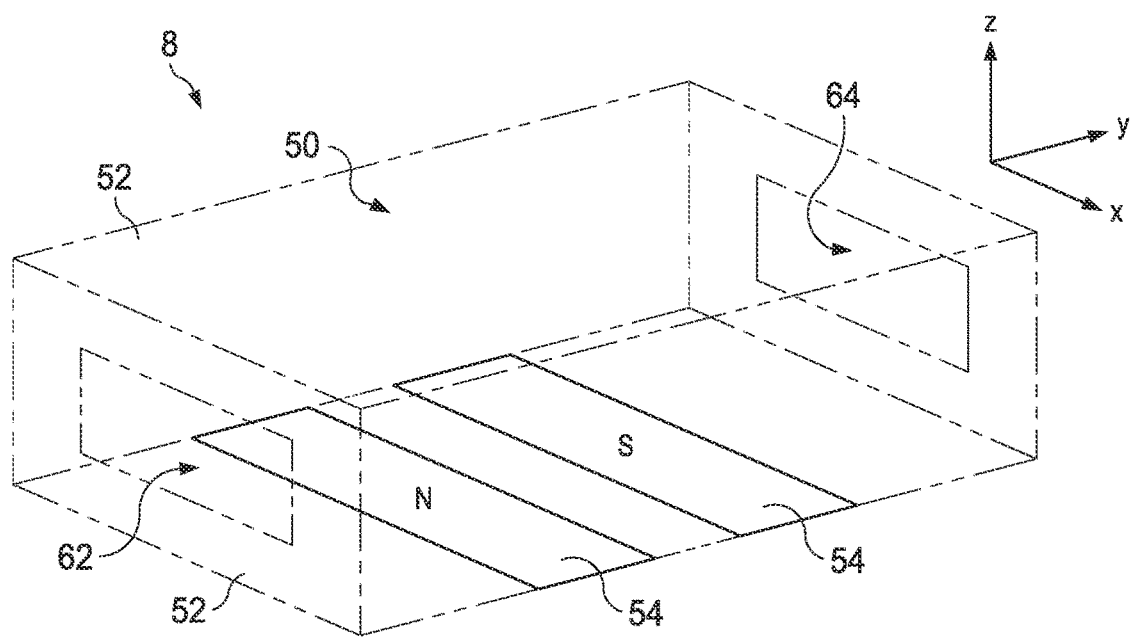
FIG. 2B is a semi-transparent, three-dimensional schematic diagram of the flow-through magnetic separation/debeading module of FIG. 2A.

FIG. 2A is a transverse cross-sectional schematic diagram of flow-through magnetic separation/debeading module 8 in an x-oriented magnet configuration, while FIG. 2B is a semi-transparent, three-dimensional schematic diagram of the same magnetic separation module 8 in the same configuration. Flow-through magnetic separation/debeading module 8 includes a flow chamber 50, defined by walls 52. External dipole magnets 54 create magnetic force lines 56. Magnets 54 are housed on movable platform 60. Flow-through magnetic separation/debeading module 8 further includes inlet 62 and outlet 64 through which a cell suspension may be flowed in the y direction through module 8.

Figure 4A:
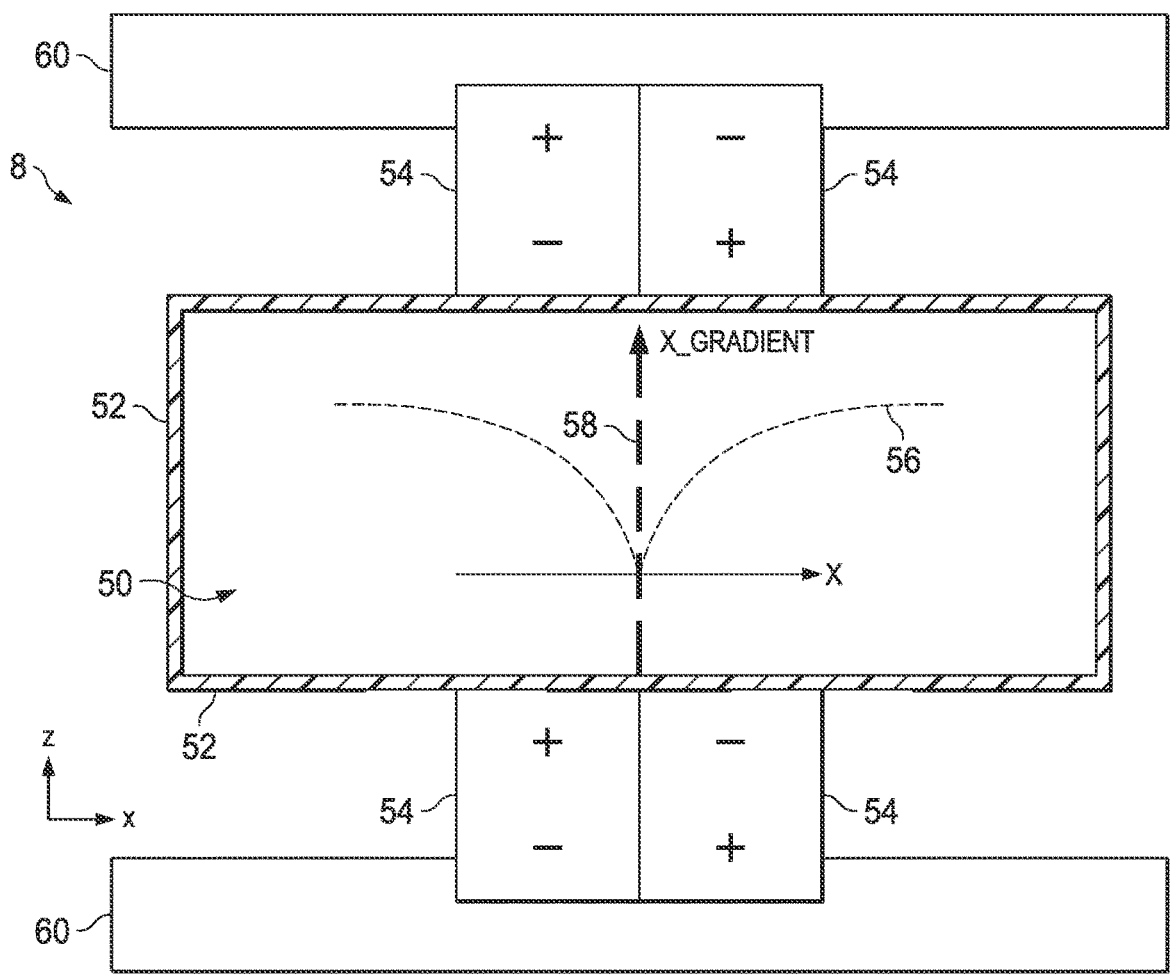
FIG. 4A is a transverse cross-sectional schematic diagram of a flow-through magnetic separation/debeading module in a zero-gradient configuration.

Although FIGS. 2A and 2B depict one array of magnets 54, flow-through magnetic separation/debeading module 8 may have two or more arrays, as shown in FIG. 4A, and may have more than two magnets in an array. In addition, magnets 54 may be in a permanent position, in which case separating/debeading module 8 may lack movable platform 60 or may have a movable flow chamber 50. Furthermore, although magnets 54 are shown in an x-oriented configuration, they can be at any angle in the x-y plane, including a y-orientation or an x-y cross-orientation.

Inlet 62 and outlet 64 may have any configuration sufficient to establish laminar flow of the cell suspension through chamber 50. Inlet geometry, outlet geometry, and flow rate all influence the flow of the cell suspension through chamber 50. Turbulent flow may be acceptable in some instances.

Walls 52 may be rigid structures, or they may be flexible. For instance, they may be the walls of a cell storage bag or other similar component. When walls 52 are flexible, the dimension of chamber 50 in the z direction may vary depending on the flow rate of the cell suspension through chamber 50.

The dimension of chamber 50 in the z direction may be between 5 μm and 100 μm, between 5 μm and 500 μm, or between 5 μm and 1000 μm, between 5 μm and 1 cm, or generally 100 μm, 500 μm, 1000 μm, or 1 cm or less. The dimensions in both the x, y, and z directions may be limited to achieve fluidic forces that are sufficiently high to move cells or paramagnetic particles through chamber 50.

Magnets 54 may have a high magnetic field strength. For instance, they may contain rare earth metals, such as neodymium or samarium alloyed with another metal, such as cobalt. Magnets 54 may be dipole magnets as depicted, or they may be other types of magnets, such as quadrapole magnets. Magnets 54 may have an adjustable magnetic field strength. For example, they may be electromagnets. Magnets 54 may be arranged to maximize magnetic attraction for magnets on the same side of chamber 50, to maximize magnetic repulsion for magnets on opposite sides of chamber 50, or both. Although FIG. 2A depicts a particular magnet configuration, configurations in which magnet polarity is opposite or concordant may be used depending upon the effect to be achieved.

Figure 3:
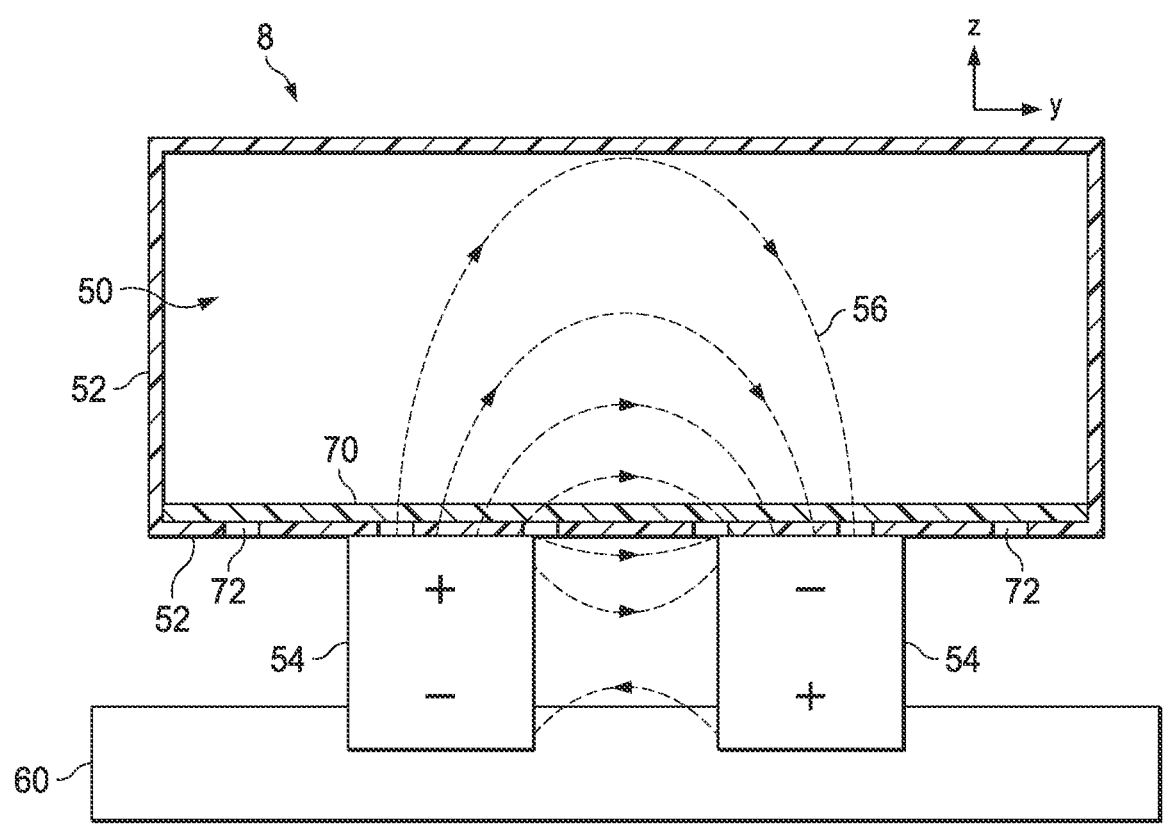
FIG. 3 is a side longitudinal cross-sectional schematic diagram of a flow-through magnetic separation/debeading module with a membrane and sub-membrane fluid injection ports.

FIG. 3 is a side longitudinal cross-sectional schematic diagram of a flow-through magnetic separation/debeading module 8 with membrane 70 located above sub-membrane fluid injection ports 72 and magnets 54. Fluid from buffer module 6 or another fluid module may be introduced through fluid injection ports 72 to help debead cells located near membrane 70.

Figure 7A:
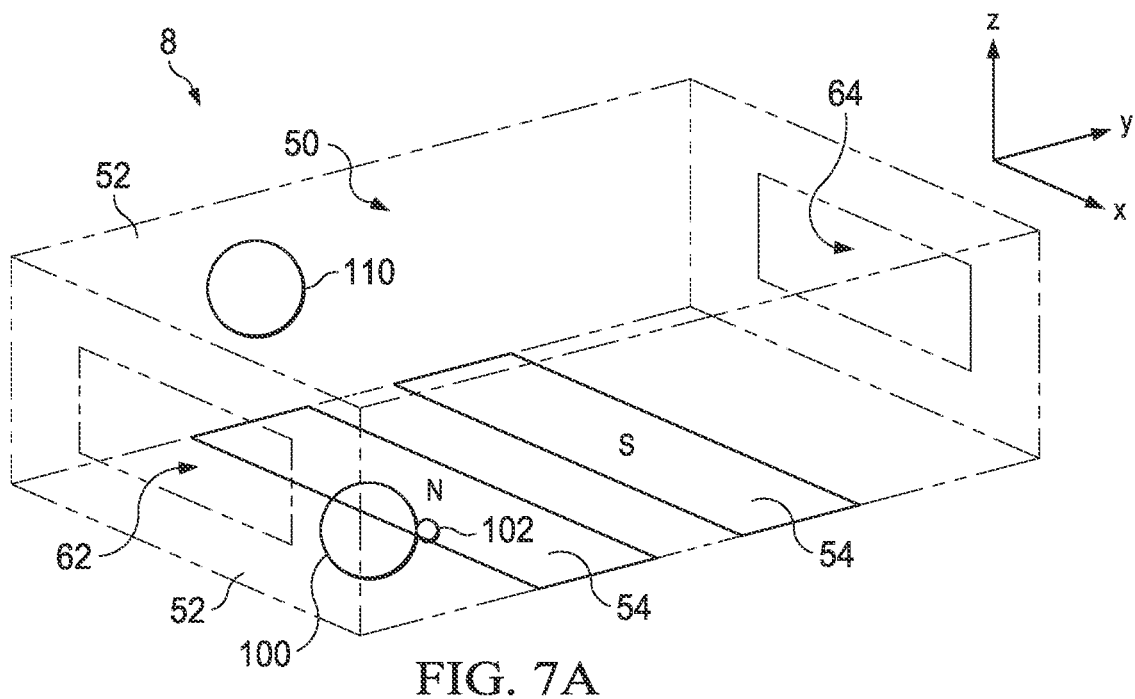
FIGS. 7A, 7B, and 7C are diagrams of the flow-through magnetic separation/debeading module of FIG. 2B with cells present during magnetic separation.
Figure 7B:
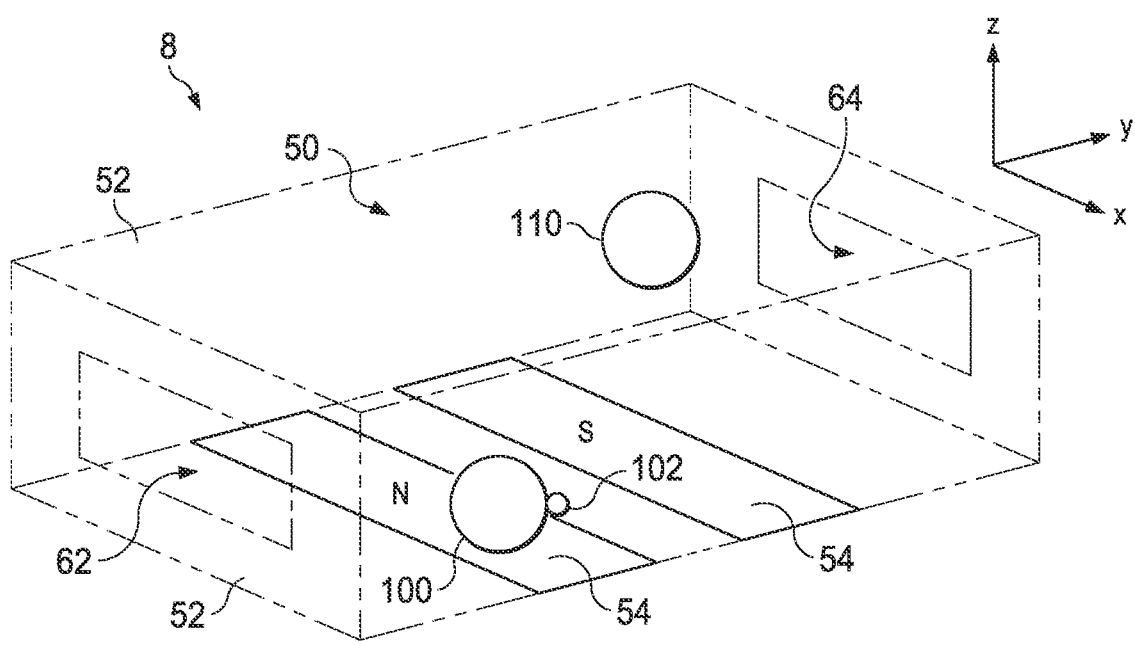
Figure 7C:
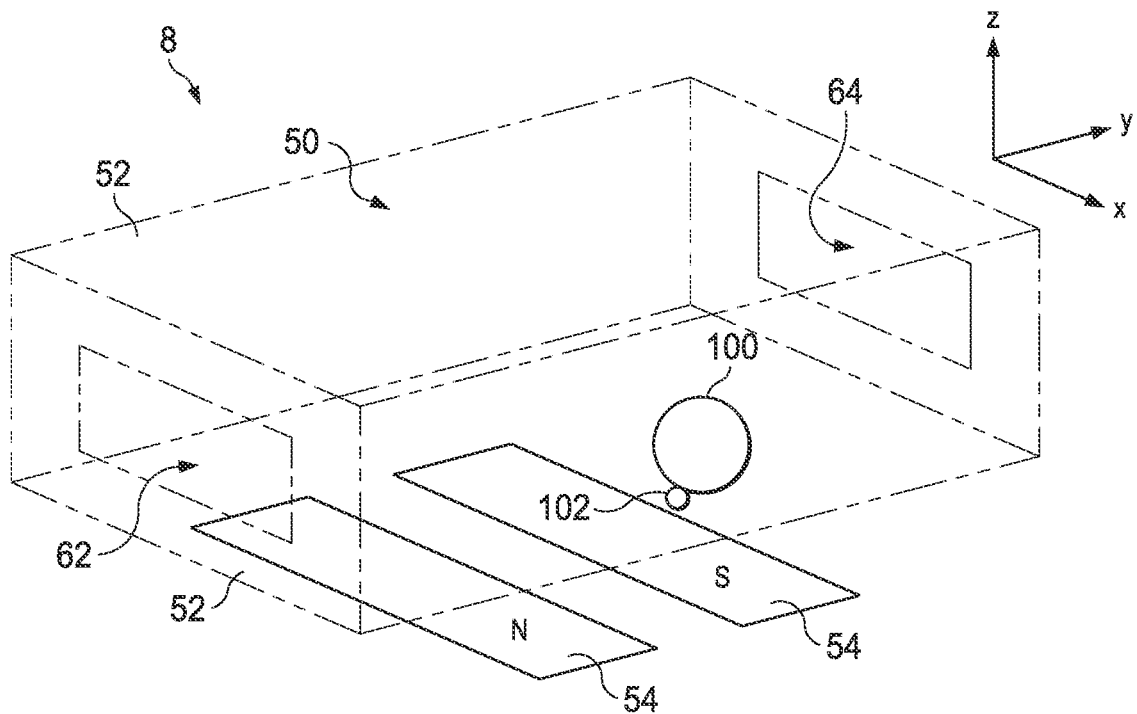

Movable platform 60 may be movable in the z direction allowing the movement of magnets 54 in the z direction from a position adjacent to chamber 50 as shown in FIGS. 2A and 2B, or proximate chamber 50 (not shown), to a position distant from chamber 50 (as shown in FIG. 7C). For example, the position distant from chamber 50 may be at least 1 cm from the nearest wall 52. The position distant is sufficient to prevent any substantial influence of magnets 54, via their magnetic fields, on any paramagnetic particle in chamber 50. The position distance may be substantially less if a magnetically insulating material is inserted between magnets 54 and chamber 50. If the magnets 54 have an adjustable magnetic field strength, rather than being moved, they may simply be adjusted to a lower magnetic field strength or zero magnetic field strength to avoid any substantial influence on any paramagnetic particles in chamber 50.

Figure 4B:
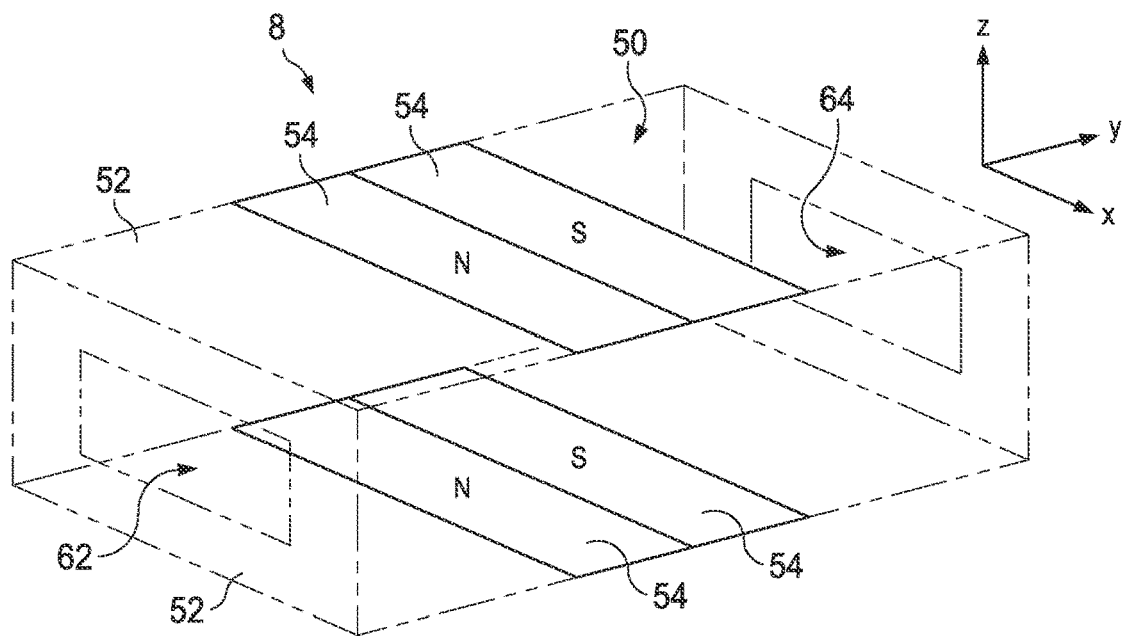
FIG. 4B is a semi-transparent, three-dimensional schematic diagram of the flow-through magnetic separation/debeading modulce of FIG. 4A.

Particularly when using a zero-gradient configuration, module 8 may have a top array of magnets 54 and a bottom array of magnets 54, as depicted in FIGS. 4A and 4B. Movable platform 60 may be rotatable in the x-y plane, or magnets 54 may be permanently oriented such that magnets 54 are in an x-y cross-oriented configuration, such as that depicted in the top longitudinal cross-sectional schematic diagram of a flow-through magnetic separation/debeading module 8 of FIG. 4C. For use in a zero-gradient configuration, flow-through magnetic separation/debeading module 8 may have two inlets 62, a non-magnetic inlet 62a and a magnetic inlet 62b as well as two outlets 64, a magnetic outlet 64a and a non-magnetic outlet 64b. In this instance, the zero gradient line 58 in an x-y cross-oriented direction forms a zero gradient filter when module 8 is in use. Inclusion of additional magnets 54 may provide two zero gradient lines, 58a and 58b in the same module 8, as illustrated in FIG. 4D, allowing the separation of different paramagnetic particles into different outlets 64a and 64b, or providing a back-up filter.

Zero gradient line 58 may be a zero gradient band, having a dimension in the x direction, if magnets 54 are spaced sufficiently apart from one another rather than being adjacent as depicted in FIGS. 2A and 2B.

Magnets for use with a flow-through magnetic separation/debeading module may be located external to the chamber that the cell suspension flows through, or internal to the chamber. If the magnets are internal, they may be coated with a biocompatible material. Particularly if the magnets are internal, they may be disposable.

Figure 1B:
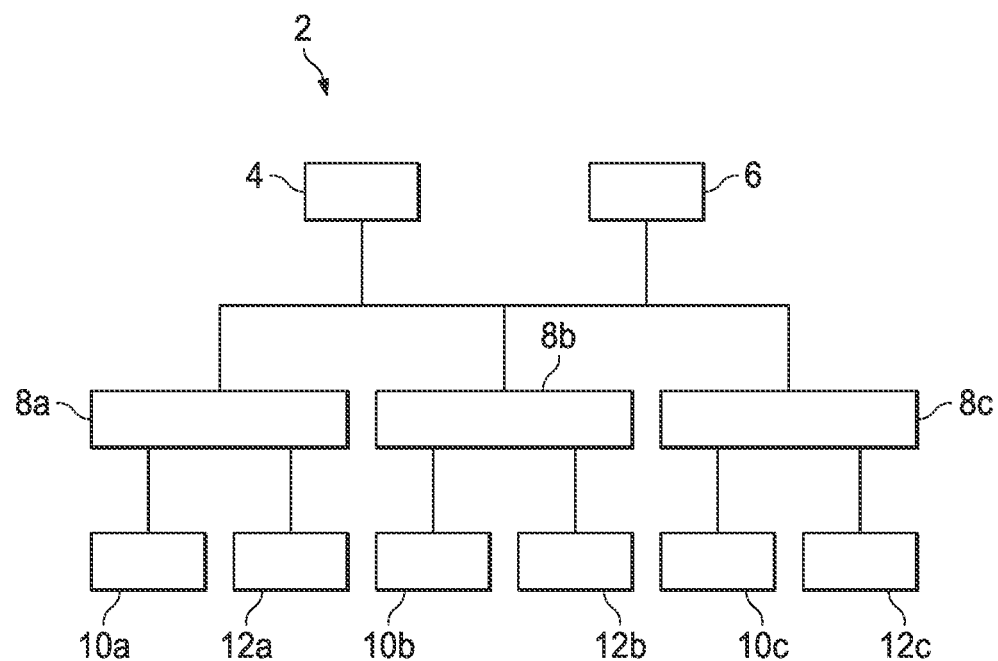
FIG. 1B is a schematic diagram of a cell processing system with a plurality of flow-through magnetic separation/debeading modules in parallel.

FIG. 1B is a schematic diagram of a cell processing system 2, which includes a plurality of flow-through magnetic separation/debeading modules 8a, 8b and 8c in parallel. Although only three flow-through magnetic separation/debeading modules 8 are illustrated, the plurality may be any number greater than two. When flow-through magnetic separation/debeading modules 8 are in parallel, the modules will typically be of the same type and in the same configuration so that the same function is performed by each. Parallel flow-through magnetic separation/debeading modules 8 may be particularly useful for rapid cell suspension processing or management of fluid volume when combined with additional modules. In addition, placing flow-through magnetic separation/debeading modules 8 in parallel provides flexibility in controlling fluid flow, as the modules need to all be used at the same time.

Figure 1C:
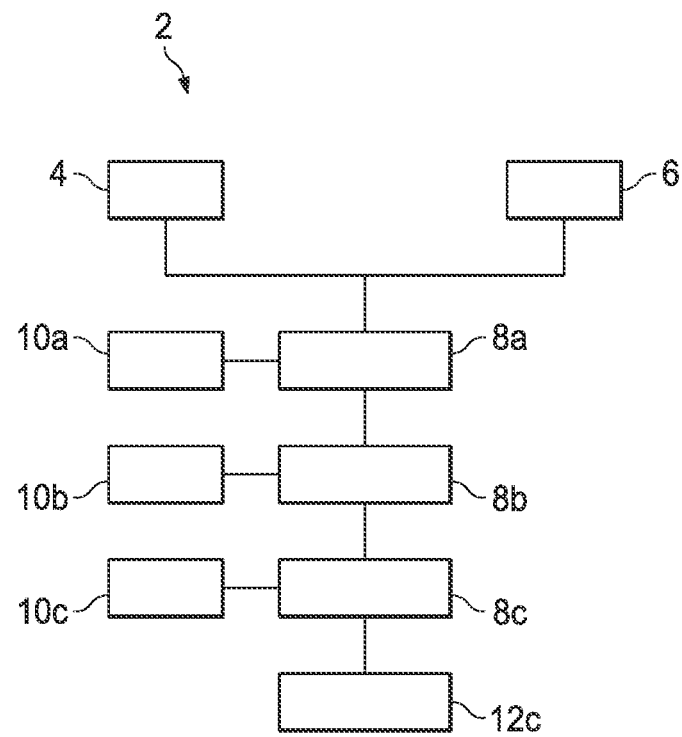
FIG. 1C is a schematic diagram of a cell processing system with a plurality of flow-through magnetic separation/debeading modules in series.

FIG. 1C is a schematic diagram of a cell processing system 2, which includes a plurality of flow-through magnetic separation/debeading modules 8a, 8b and 8c in series. Although only three flow-through magnetic separation/debeading modules 8 are illustrated, the plurality may be any number greater than two. When flow-through magnetic separation/debeading modules 8 are in series, they may be of the same type and configuration so that the same function is performed by each, but, typically, they will be of different types and configurations so that different functions are performed by each. For instance module 8a may separate paramagnetic particle-bound cells and unbound cells, module 8b may debead paramagnetic particle-bound cells, and module 8c may debead paramagnetic particle-bound cells under greater magnetic field gradients.

Figure 1D:
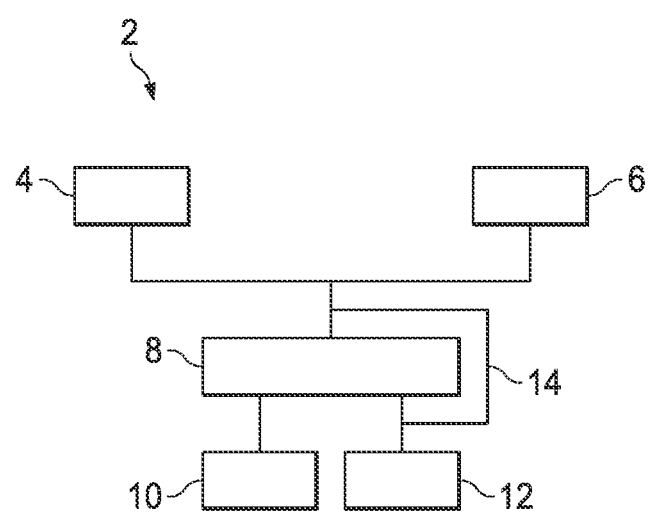
FIG. 1D is a schematic diagram of a cell processing system with a return loop.

FIG. 1D is a schematic diagram of a cell processing system 2 in which return loop 14 directs paramagnetic particle-bound cells back through flow-through magnetic separation/debeading module 8. Such a system may be used to achieve better separation of paramagnetic particle-bound cells and unbound cells, or better debeading or separation of unbound cells and paramagnetic particles as compared to a similar system with no return loop 14. Fluid may be directed to return loop 14 or to magnetic output module 12 by a valve or switch.

Figure 1E:
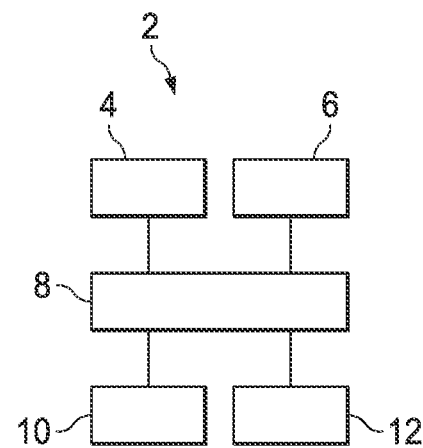
FIG. 1E is a schematic diagram of a cell processing system with cell suspension and buffer modules separately connected to the flow-through magnetic separation/debeading module.

FIG. 1E is a schematic diagram of a cell processing system 2 in which cell suspension module 4 and buffer module 6 are separately connected to flow-through magnetic separation/debeading module 8. Such a system may be particularly useful when flow-through magnetic separation/debeading module 8 has two inlets 62 and two outlets 64 and magnets 54 in an x-y cross-oriented configuration as shown in and described with respect to FIG. 5.

Figure 1F:
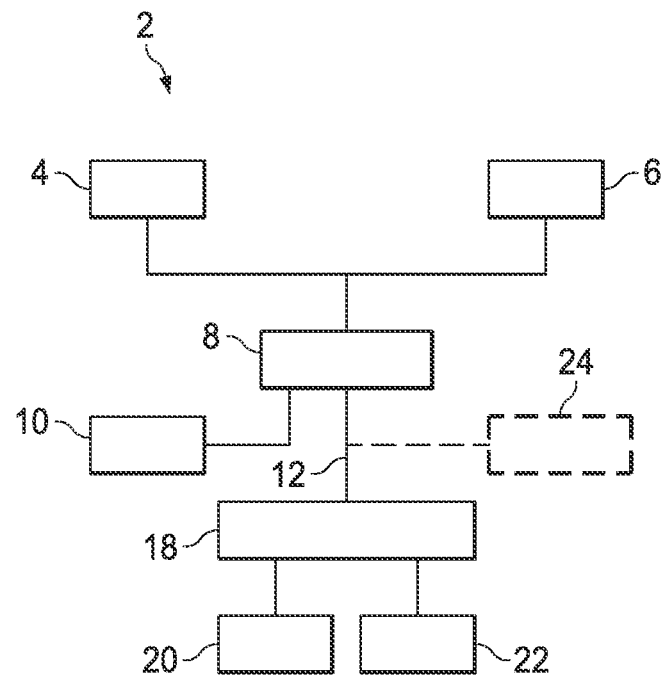
FIG. 1F is a schematic diagram of a cell processing system including a spinning membrane debeading module.

FIG. 1F is a schematic diagram of a cell processing system 2 with a spinning membrane debeading module 18 located downstream of flow-through magnetic separation/debeading module 8. Spinning membrane debeading module 18 is connected to waste output module 20 and cell output module 22. In this system 2, flow-through magnetic separation/debeading module 8 separates paramagnetic particle-bound cells and unbound cells, while a spinning membrane debeading module 18 conducts all debeading, or flow-through magnetic separation/debeading module 8 may conduct debeading as well. Reagent module 24 may optionally be present if a reagent, such as a chemical agent, is added to the suspension fluid in spinning membrane debeading module 18. Although one spinning membrane debeading module 18 is illustrated in FIG. 1F, system 2 may include a plurality of modules 18 in series or in parallel. When modules 18 are in series, a chemical agent may only be added to the last module 18 to minimize cell exposure to the chemical agent.

The reagent in reagent module 24 may be any chemical agent that weakens the bond between a particle and a cell. The particle may be the paramagnetic particle, or it may be a non-paramagnetic particle.

Figure 5A:
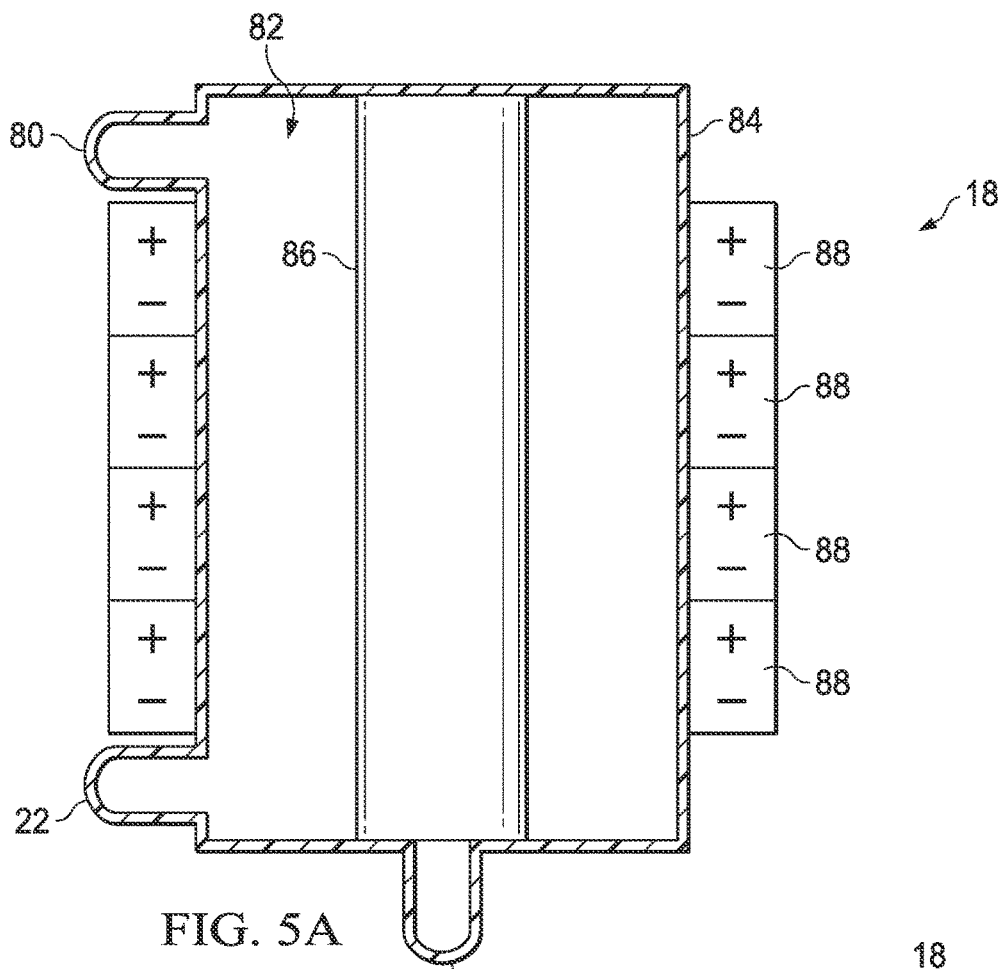
FIG. 5A is a longitudinal cross-sectional schematic diagram of a spinning membrane debeading module.

FIG. 5A is a longitudinal cross-sectional schematic diagram of a spinning membrane debeading module 18. This module 18 includes sample inlet 80, which allows a cell suspension fluid to flow into cylindrical debeading chamber 82, which is defined in party by cylindrical side-wall 84 and contains co-axially oriented cylindrical spinning membrane 86. Wall 84 is lined on the exterior with magnets 88. Debeading chamber 18 allows fluid that has passed through spinning membrane 86 to exit via waste output module 20, while the remaining fluid and cells exit through cell output module 22. Spinning membrane 86 has an average pore size smaller than the average diameter of the cells, but larger than any non-paramagnetic particle to be removed by debeading. The average pore size may also be larger than any paramagnetic particle to be removed, allowing removal of these paramagnetic particles by the spinning membrane either as a primary particle removal method, or as a back-up to magnetic removal.

Figure 5B:
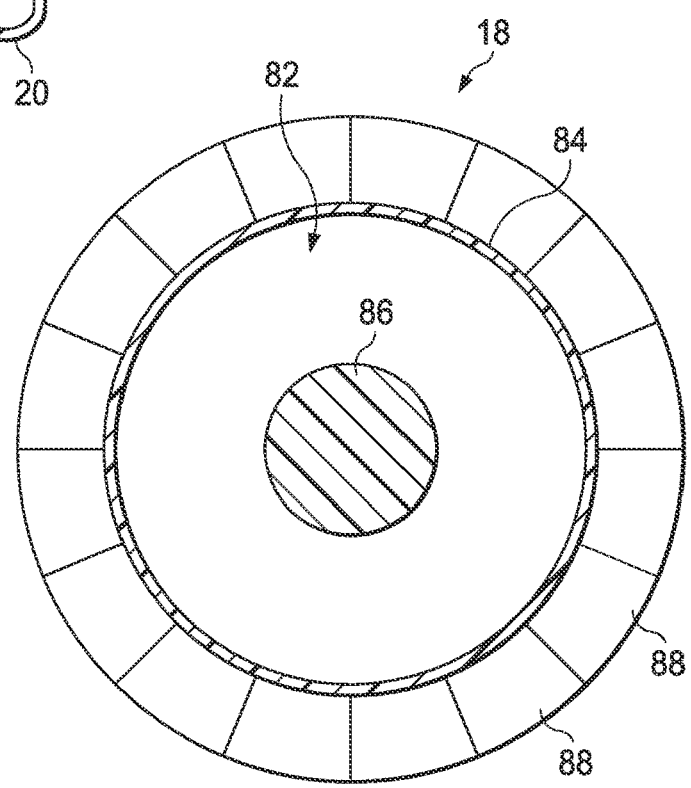
FIG. 5B is a transverse cross-sectional schematic diagram of a spinning membrane debeading module with a first magnet configuration.
Figure 5C:
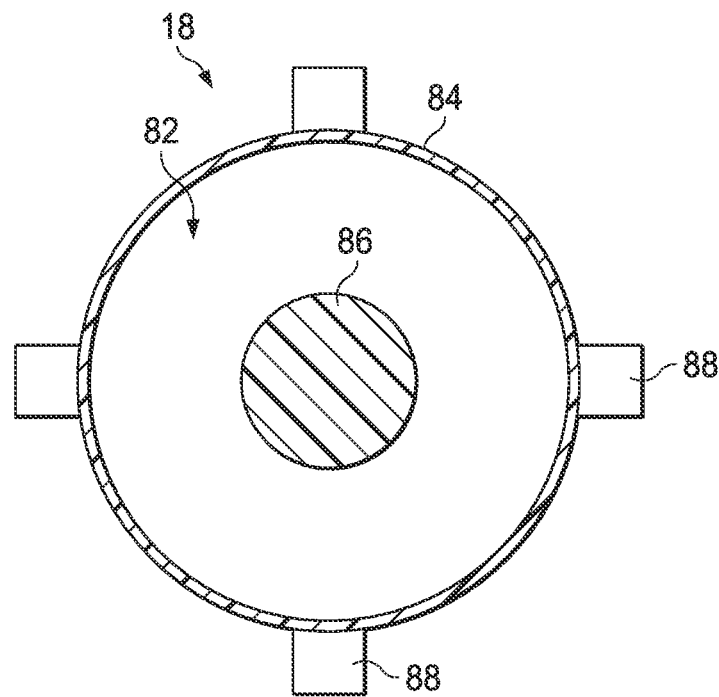
FIG. 5C is a transverse cross-sectional schematic diagram of a spinning membrane debeading module with a second magnet configuration.

Magnets 88 may substantially surround wall 84 as shown in FIG. 5B, or they may be spaced at intervals along wall 84, as shown in FIG. 5C. Magnets 88 may be mounted on a movable platform to allow them to be moved from a position adjacent to wall 88, as shown in FIGS. 5A-5C, or proximate walls 88 (not shown) to a position distant from wall 84. For example, the position distant may be at least 1 cm from wall 84. This movement to a position distant prevents magnets 88, via their magnetic field, from having a substantial influence on any paramagnetic particles in chamber 82. If a magnetically insulating material is inserted between magnets 88 and chamber 82, the position distant may be less than if the magnetically insulating material were not present. If the magnets 88 have an adjustable magnetic field strength, rather than being moved, they may simply be adjusted to a lower magnetic field strength or zero magnetic field strength to avoid an substantial influence on any paramagnetic particles in chamber 82.

Although multiple magnets 88 are shown in FIG. 5, it is possible to have only a single magnet 88.

Magnets 88 may have a high magnetic field strength. For instance, they may contain rare earth metals, such as neodymium or samarium alloyed with another metal, such as cobalt. Magnets 88 may be dipole magnets, quadrapole magnets, or any other type of magnets. Magnets 88 may have an adjustable magnetic field strength, for example, they may be electromagnets. Magnets 88 may be arranged to maximize magnetic attraction, for instance in a wrapped configuration.

Magnets for use with a spinning membrane module may be located external to the chamber that the cell suspension flows through, or internal to the chamber. If the magnets are internal, they may be coated with a biocompatible material. Particularly if the magnets are internal, they may be disposable.

Example spinning membranes suitable for use in modules disclosed herein include the 4-μm track-etched polycarbonate spinning membrane used in the LOVO® cell processing system (Fresenius Kabi, Fenwal, Lake Zurich, Ill.), and the spinning membrane used in the ISOLEX® magnetic cell separation systems (Baxter, Deerfield, Ill.).

Elements from FIGS. 1A-1F, including flow-through magnetic separation/debeading modules 8 as described in FIGS. 2-4 or magnetic spinning membrane debeading modules 18 as described in FIG. 5 may be combined with one another in cell processing system 2 depending on the specific cell processing to be performed. The elements may be combined as depicted, or in other reasonable variations. For instance, a reagent module 24 may be included in a system otherwise a depicted in FIG. 1A so that a chemical agent may be added to suspension fluid in flow-through magnetic separation/debeading module 8 when it is used for debeading. Modules, including additional buffer modules or output modules, may be arranged and used to ensure proper fluid volumes and flow rates, particularly in modules 8 and 18.

Figure 1G:
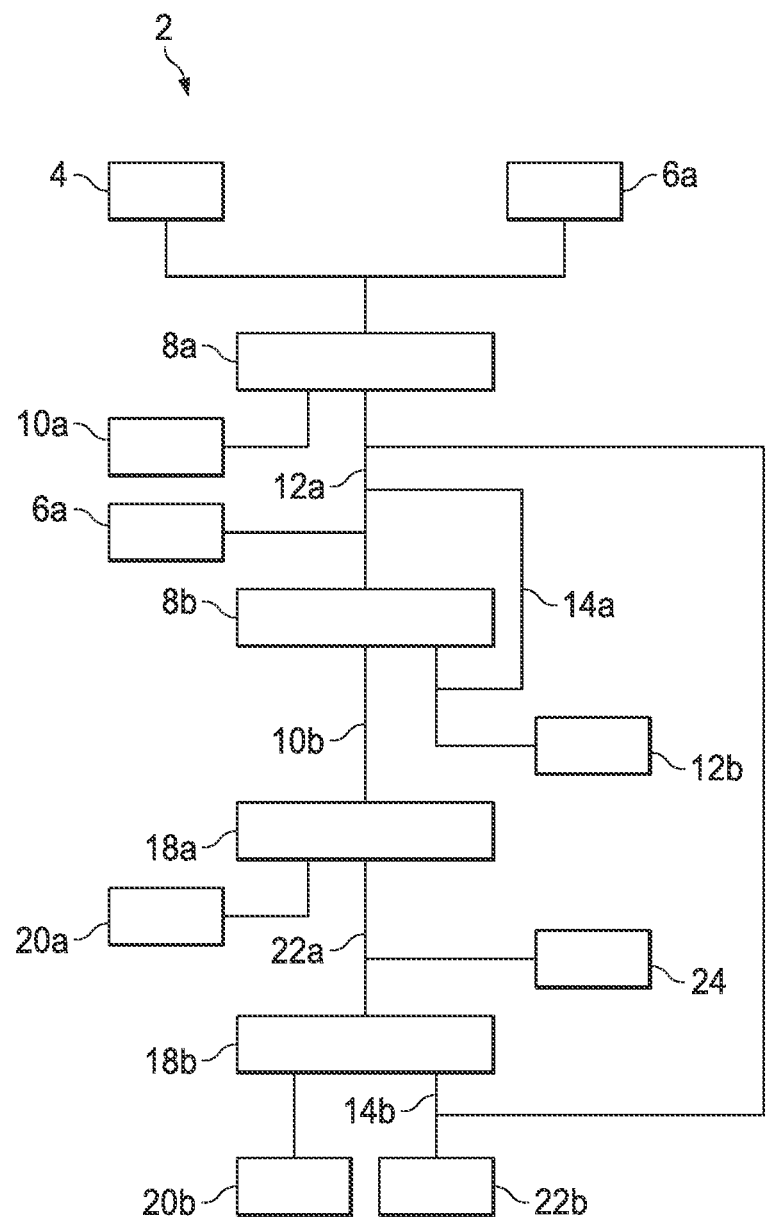
FIG. 1G is a schematic diagram of a cell processing system including multiple flow-through magnetic separation/debeading modules and multiple spinning membrane debeading modules.
Figure 1H:
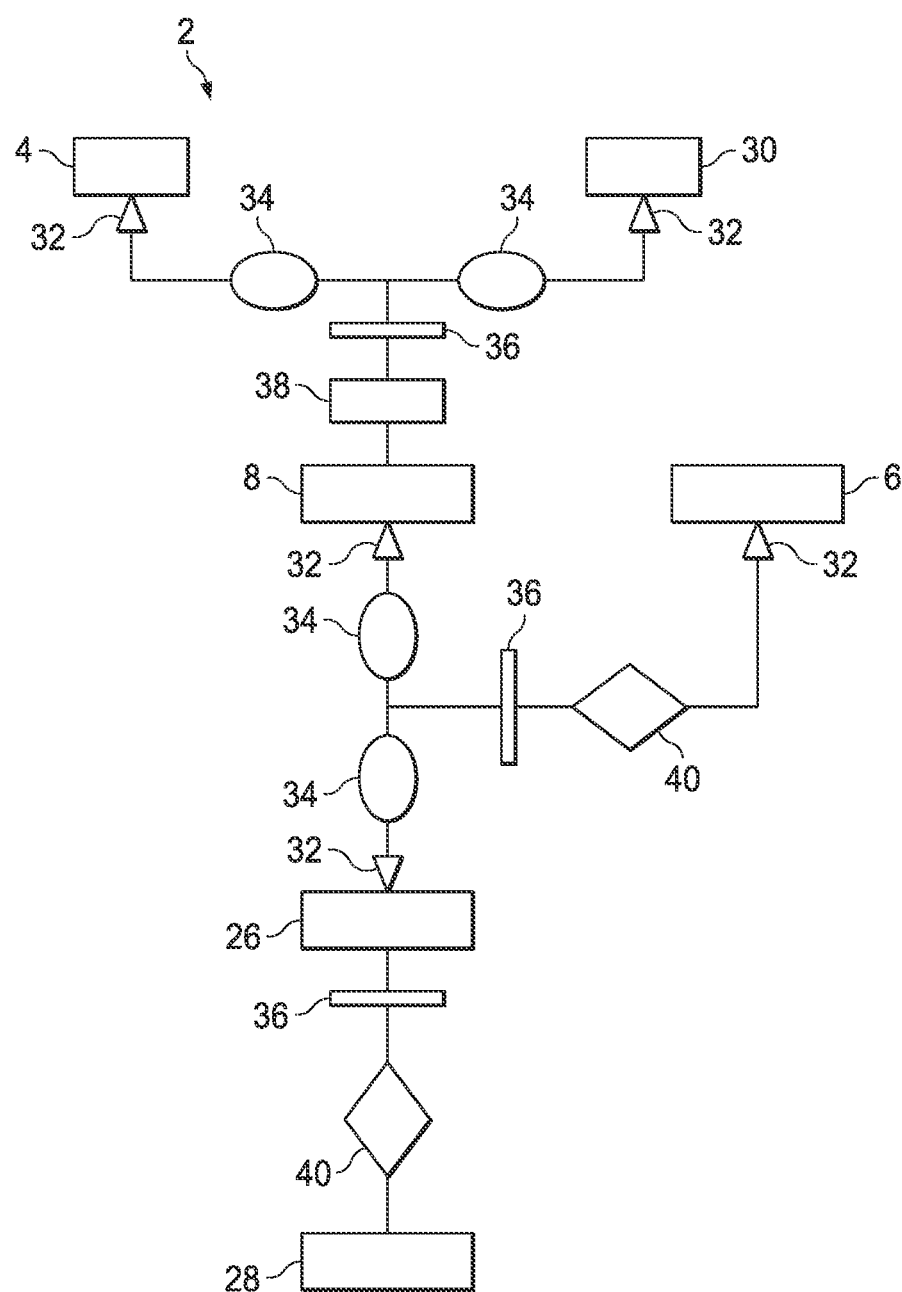
FIG. 1H is another schematic diagram of a cell processing system with a flow-through magnetic separation/debeading module.

One example cell processing system 2 combining multiple modules and loops is illustrated in FIG. 1G. This system includes cell suspension module 4 and buffer module 6a connected to first flow-through magnetic separation/debeading module 8a, which has non-magnetic output module 10a and magnetic output module 12a. Magnetic output module 12a is connected to second, in-series flow-through magnetic separation/debeading module 8b, which is also connected to buffer module 6b and has non-magnetic output module 10b and magnetic output module 12, and return loop 14a. Return loop 14a leads back to module 8b. Magnetic output module 12b leads to first spinning membrane debeading module 18a, which has waste output module 20a and cell output module 22a. Cell output module 22a leads to second, in-series spinning membrane debeading module 18b, which is also connected to reagent module 24 as well as waste output module 20b, return loop 14b, and cell output module 22b. Return loop 14b leads back to second, in-series flow-through magnetic separation/debeading module 8b.

Another example cell processing system 2, having various additional modules with specific fluid conduits, is shown in FIG. 1H. Cell suspension module 4 and satellite module 30, which may be empty or may contain buffer, are connected to flow-through magnetic separation/debeading module 8. Flow-through magnetic separation/debeading module 8 is separately connected to buffer module 6 and reservoir module 26. Reservoir module 26 is further connected to recovery module 28. Many connections are made using spike tubing 32. The system further contains, along various fluid conduits, roller clamps 34, weld sites 36, a slide clamp 38, and pinch clamps 40.

Cell processing system 2 may contain a variety of additional modules 16, such as magnetic columns, other physical separation modules, cell washing modules, cell concentration modules, and media exchange modules.

Cell Separation and Debeading Methods

System 2 may be used to separate paramagnetic particle-bound cells and unbound cells, to debead magnetic-particle bound cells, to separate paramagnetic particles and unbound cells, or any combination thereof, in a flow-through process. In a flow-through process, all cells continue to move while in flow-through magnetic separation/debeading module 8. None, no more than 0.01%, or no more than 0.05%, or no more than 1% of paramagnetic particle-bound cells passing through module 8 stop along walls 52.

Flow-Through Magnetic Separation/Debeading Processes

In a flow-through process using the system of FIG. 1A, flow-through magnetic separation/debeading module 8 may optionally be primed by flowing buffer from buffer module 6 through it to either non-magnetic output module 10 or magnetic output module 12, or another output or additional module 16. A cell suspension containing paramagnetic particle-bound cells is flowed through module 8.

If system 2 is configured for separation, the cell suspension is directed to non-magnetic output module 10. Module 8 may periodically be configured to not attract paramagnetic particles while buffer from buffer 6 flows through it to magnetic output module 12. In order to ensure better separation of cells, and high purity of the magnetic or non-magnetic cell products, the cell suspension may be directed through a loop 14 for a second or subsequent passage through module 8. Paramagnetic particle-bound cells may be directed to an additional component 16, such as a flow-through magnetic separation/debeading module 8 configured for debeading or to a spinning membrane debeading module 18.

If system 2 is configured for debeading, after flowing through module 8, the cell suspension is directed to non-magnetic output module 10. Alternatively, the cell suspension may be directed through loop 14 for a second or subsequent passage through module 8 prior to direction to non-magnetic output module 10.

Figure 6:
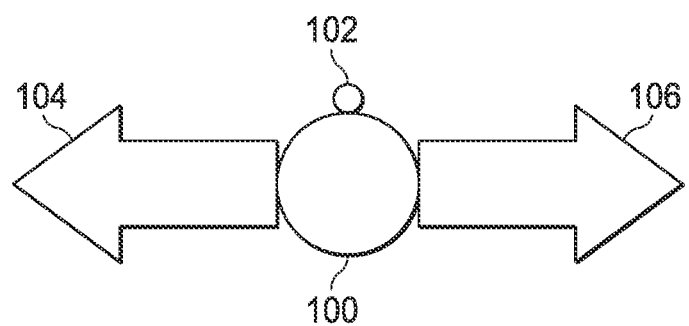
FIG. 6 is diagram of fluidic force and magnetic force on a cell.

Processes using flow-through magnetic separation/debeading module 8 subject each paramagnetic particle-bound cell 100 with at least one bound paramagnetic particle 102 to a fluidic (shear or drag) force 104. Each cell 100 is also subjected to magnetic force 106, as shown in FIG. 6. Fluidic force 104 and magnetic force 106 may be combined in such a way that paramagnetic particle 102 remains bound to paramagnetic particle-bound cell 100, allowing cell 100 to be separated form unbound cells. Fluidic force 104 and magnetic force 106 may also be combined in such a way as to cause paramagnetic particle 102 to detach from paramagnetic particle-bound cell, allowing debeading of cell 100. Secondary forces, such a diffusion and gravity, also act upon paramagnetic particle 102, but their effects on debeading are typically much less than fluidic force and magnetic force and are often ignored when calculating the proper flow rate through a module.

System 2 may generally be configured so that, as quickly as possible, desirable cells are no longer subject to passage through modules, reducing trauma to the cells. For instance, only the magnetic output module 12 may contain a return loop to flow-through magnetic separation/debeading module 8 in a debeading configuration, allowing more easily debeaded cells to pass through module 8 fewer times than those with more recalcitrantly bound paramagnetic particles.

Flow-through module 8 may be laminar or turbulent. Magnetic force 106 is influenced by the saturation flux (ms) of paramagnetic particle 102. Magnetic force 106 is also influenced by the strength of the magnetic field 56 to which paramagnetic particle 102 is subjected, which is influenced by the strength of magnets 54 as well as depth of chamber 50 in the z direction and cell 100's location within that chamber. Magnetic force 106 is further influenced by the magnetic field gradient to which paramagnetic particle 102 is subjected as it moves through chamber 50, which is influenced by the strength and placement of magnets 54 as well as paramagnetic particle 102's location with respect to magnets 54.

In addition, fluidic forces are affected by the fluid flow velocity, which is typically highest in the center of the chamber and zero at the walls, meaning that cells attached to the walls may not experience sufficient fluidic force to detach them from their paramagnetic particle and that cells along the wall may be largely stationary and may shield downstream cells from fluidic forces. This results in loss of desirable cells and is avoided by continuous flow of the cell suspension through chamber 50. This loss may be avoided by a flow-through approach, in which cells are not rendered stationary by magnetic force. It may also be avoided by modules in which velocity is not zero or near zero at the walls, such as plug flow modules where fluid flow velocity is uniform across the chamber.

Flow-through Separation Process

A flow-through separation process may be conducted using flow-through magnetic separation/debeading module 8 in a configuration as shown in FIGS. 2A and 2B. Flow rate is such that fluidic force 104 and magnetic force 106 allow paramagnetic particle 102 to remain bound to cell 100. Flow rate is also such that cell 100 is not lysed by fluidic forces.

FIG. 7A shows module 8 of FIG. 2B when paramagnetic particle-bound cell 100 and unbound cell 110 have recently entered chamber 50. In FIG. 7B, cell 100 has stopped, while unbound cell 110 has continued on at it original velocity. In FIG. 7C, the magnets have been moved away and cell 100 continues to move, but unbound cell 110 has exited chamber 50.

Suspension fluid exiting chamber 50 while magnets 54 are adjacent to or proximate chamber 50 enters non-magnetic output module 10. Periodically, cell suspension flow from cell suspension module 4 is stopped and buffer is flowed into chamber 50 from buffer module 6 while magnets 54 are moved away from chamber 50 to allow paramagnetic particle-bound cells 100 to be flushed into magnetic output module 12 by the buffer.

This flow-through separation process, particularly when repeated to allow multiple passages of cells through module 8, may remove at least 80%, at least 90%, at least 95%, or at least 99% of paramagnetic particle-bound cells 100 from the cell suspension prior to its entry into non-magnetic output module 10. Efficiency may be lower for a single pass process, in which cells pass through module 8 only once. For instance, in a single pass process, module 8 may remove at least 25% or at least 50% of paramagnetic particle-bound cells 100 from the cell suspension prior to its entry into non-magnetic output module 10. Single or multiple passes of either the non-magnetic output or the magnetic output through flow-through magnetic separation/debeading module 8 may result in paramagnetic particle-bound cell product with no more than 1% unbound cells 110 and containing at least 99% of the paramagnetic particle-bound cells 100 found in the cell suspension prior to the flow-through separation process, an unbound cell product with no more than 1% paramagnetic particle-bound cells 100 and containing at least 99% of the unbound cells 110 found in the cell suspension prior to the flow-through process, or both.

Flow-Through Debeading Process

A flow-through debeading process may also be conducted using flow-through magnetic separation/debeading module 8 in a configuration as shown in FIGS. 2A and 2B. Flow rate is such that fluidic force 104 and magnetic force 106 detach, on average over the cells in the cell suspension, at least one paramagnetic particle 102 from cell 100 while cell 100 passes through chamber 50. Flow rate is also such that the cells are not lysed by fluidic forces.

Figure 8A:
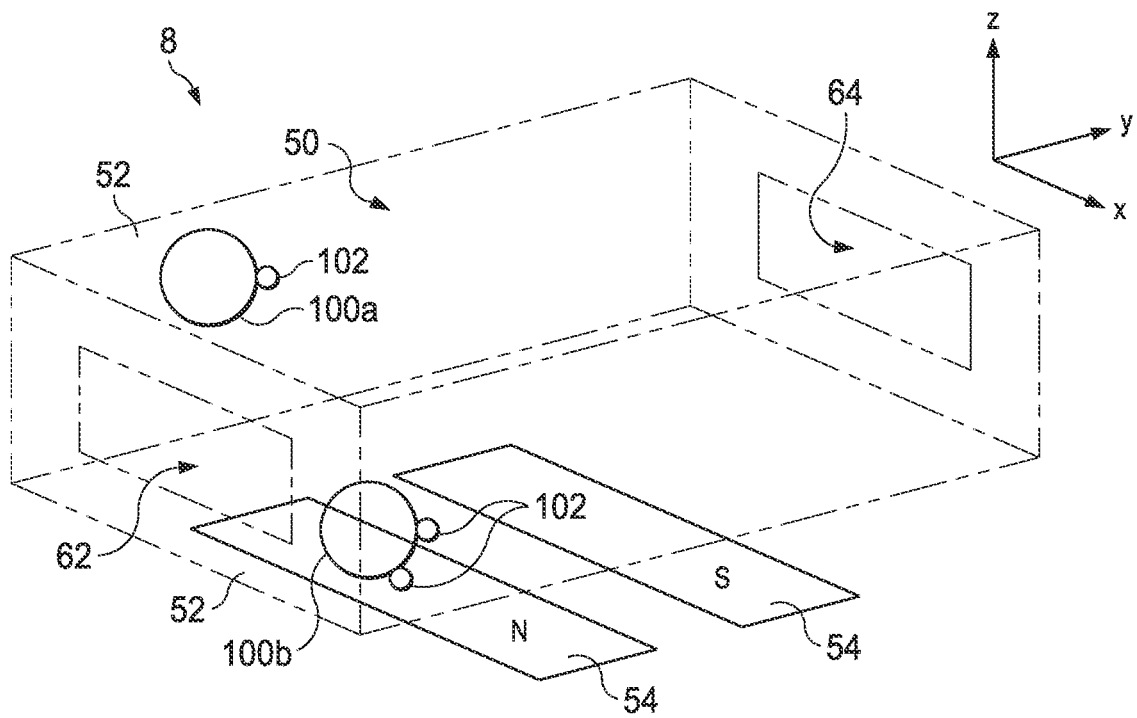
FIGS. 8A and 8B are diagrams of the flow-through magnetic separation/debeading module of FIG. 2B with cells present during magnetic debeading.
Figure 8B:
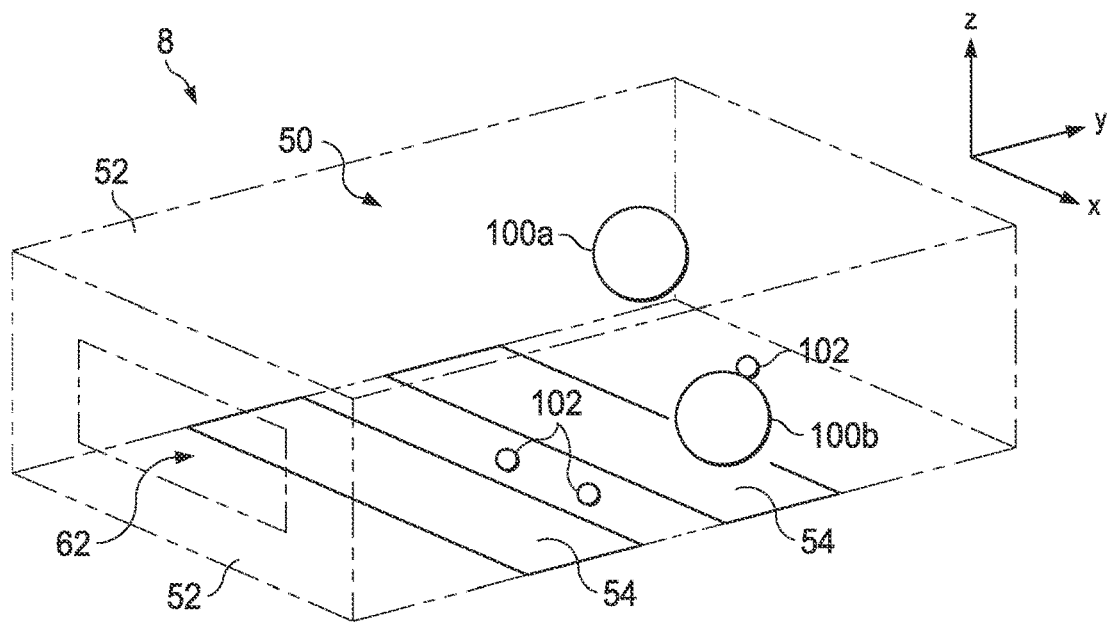

FIG. 8A shows module 8 of FIG. 2B when paramagnetic particle-bound cells 100a and 100b have recently entered chamber 50. Cell 100a has one paramagnetic particle 102, while cell 100b has two paramagnetic particles 102. In FIG. 8B, one paramagnetic particle 102 each has detached from both cell 100a and cell 100b and has come to rest on wall 52, while cells 100a and 100b continue to pass through chamber 50. Cell 100a no longer has any paramagnetic particles 102, while cell 100b retains one paramagnetic particle 102. Cell 100b may be passed through module 8a second time to remove this second paramagnetic particle 102. Alternatively, module 8 may be configured such that cell 100b remains in chamber 50, similar to the paramagnetic particle-bound cell in FIG. 7, while cell 100a passes out of chamber 50.

This flow-through debeading process may remove at least 99% of paramagnetic particles from cells.

Figure 9:
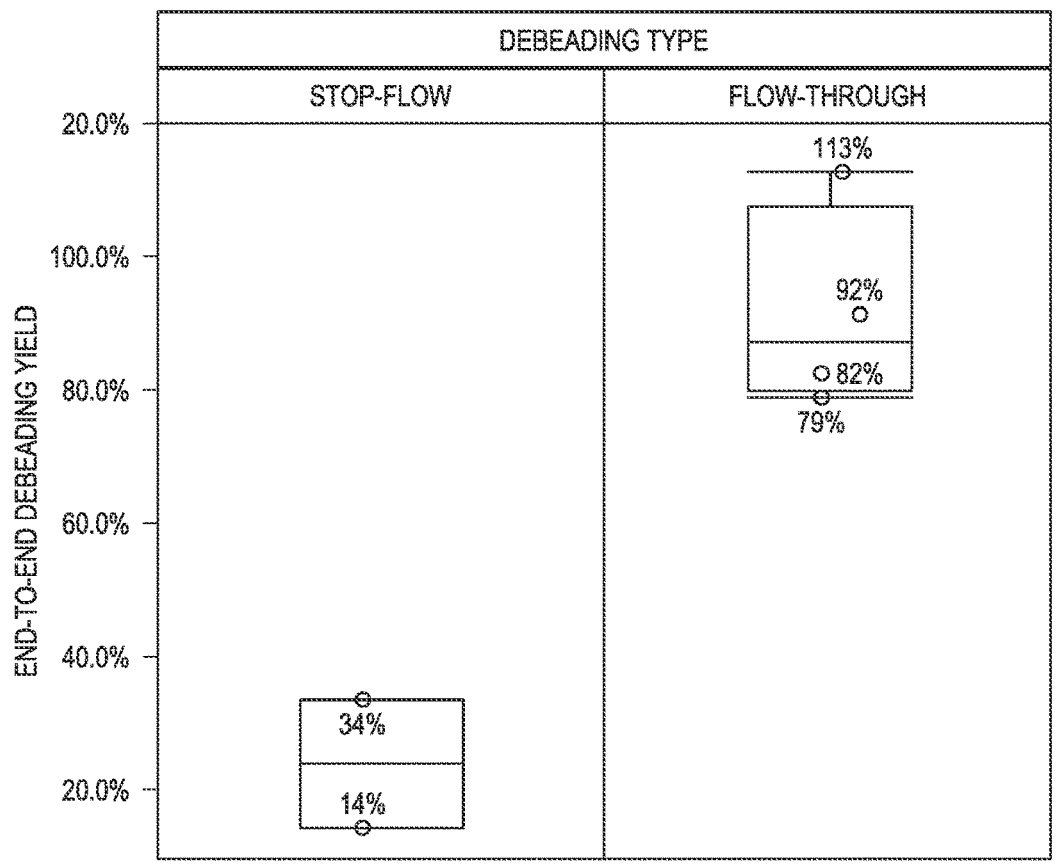
FIG. 9 is a graph comparing the results of debeading using the flow-through magnetic separation/debeading module of FIGS. 2A and 2B and the results of debeading using a conventional stop-flow module (boxes represent quartiles and the median)

When a system 2 containing a recirculation loop 14 from magnetic output module 12 was used to debead CLT0119 T cells, cells in the magnetic output were resuspended in buffer from buffer module 6 and passed through module 8 a second time and then again a third time. A comparison of the results of this process to the results of a conventional stop-flow process are provided in FIG. 9. FIG. 9 presents end-to-end yields, which are the ratios of the number of cells in the final product to the number of cells that entered the debeading system.

The flow-through magnetic separation/debeading module 8 shown in FIG. 3 may be used to debead cells in a manner similar to module 8 as shown in FIGS. 2A and 2B. Fluid introduced through ports 72 supplies a force to cells 100 sufficient to dislodge them from membrane 70. Because velocity of the suspension fluid approached zero near membrane 70, these cells might otherwise not be separated or debeaded or may be lost.

This flow-through debeading process may also remove at least 99% of paramagnetic particles from the cells.

Flow-through Zero Gradient Filter Process

A flow-through separation process may be conducted using flow-through magnetic separation/debeading module 8 in a configuration as shown in FIGS. 4A and 4B. Flow rate is such that fluidic force 104 and magnetic force 106 allow paramagnetic particle 102 to remain bound to cell 100. Flow rate is also such that cell 100 does not stop in chamber 50 and also is not lysed by fluidic forces. Various configurations are shown in FIGS. 10-13 and may be modified, for example to adjust the number and proportional size of inlets 62 and outlets 64, for use with different zero gradient filter processes. For instance, the same effects achieve by having inlets 62 and outlets 64 of different sizes can also be the achieved by providing different flow rates, typically controlled by pumps, through same-size inlets and outlets.

Figure 10A:
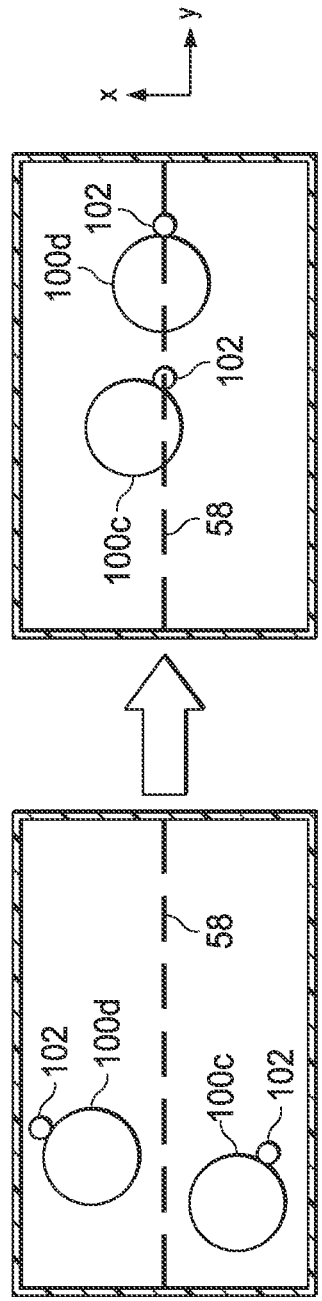
FIG. 10A is a top longitudinal x-y cross-sectional schematic diagram of a flow-through magnetic separation/debeading module with paramagnetic particle-bound cells present near the module inlet (left) and near the module outlet (right)
Figure 10B:
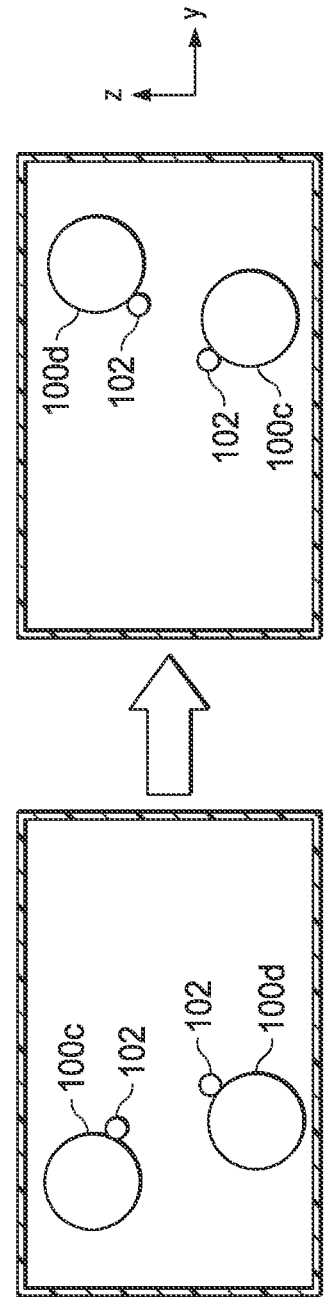
FIG. 10B is a side longitudinal cross-sectional schematic diagram of a flow-through magnetic separation/debeading module with paramagnetic particle-bound cells present near the module inlet (left) and near the module outlet (right)

FIG. 10 presents a basic description of how paramagnetic particle-bound cells 100 flow-through module 8 in a zero gradient configuration. As illustrated in FIG. 10A, cells 100 after entering module 8 (left figure) are pulled in the x-direction to zero gradient line 58 by the time it they are nearly exiting module 8 (right figure). As illustrated in FIGS. 10A and 10B, cells 100 are not subject to magnetic force effects in the y-direction or the z-direction when entering module 8 (left figure) or even when close to exiting (right figure).

Figure 11:
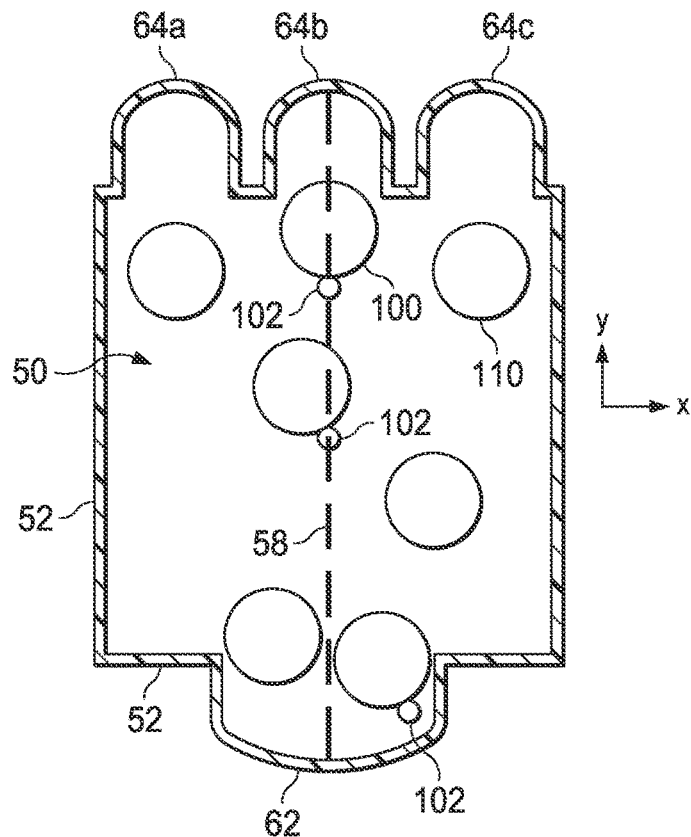
FIG. 11 is a diagram of the flow-through magnetic separation/debeading module similar to that of FIG. 4A during magnetic separation of paramagnetic particle-bound cells and unbound cells.

FIG. 11 shows a zero-gradient module 8 with magnets 54 oriented as shown in FIG. 4A. In this module, fluid enters via inlet 62. Cells 100 with magnetic particles 102 follow zero gradient line 58 and are directed to magnetic outlet 64b. Unbound cells 110 are unaffected by zero gradient line 58 and flow to non-magnetic outlets 64a and 64c. Some unbound cells 110 will also enter magnetic outlet 64b in this configuration.

Figure 4C:
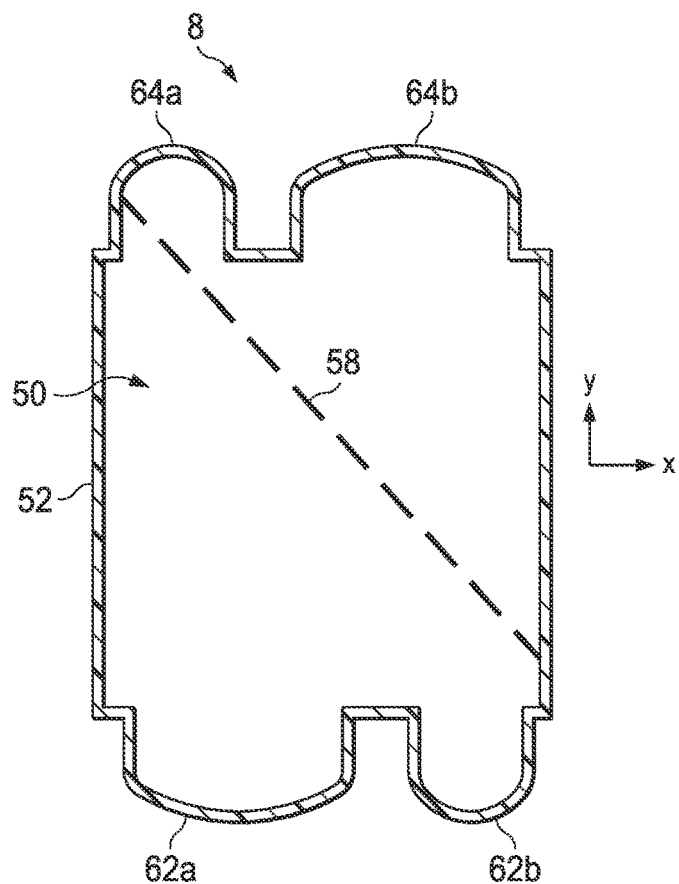
FIG. 4C is a top longitudinal cross-sectional schematic diagram of a flow-through magnetic separation/debeading module in a zero-gradient configuration to create a zero gradient filter.
Figure 4D:
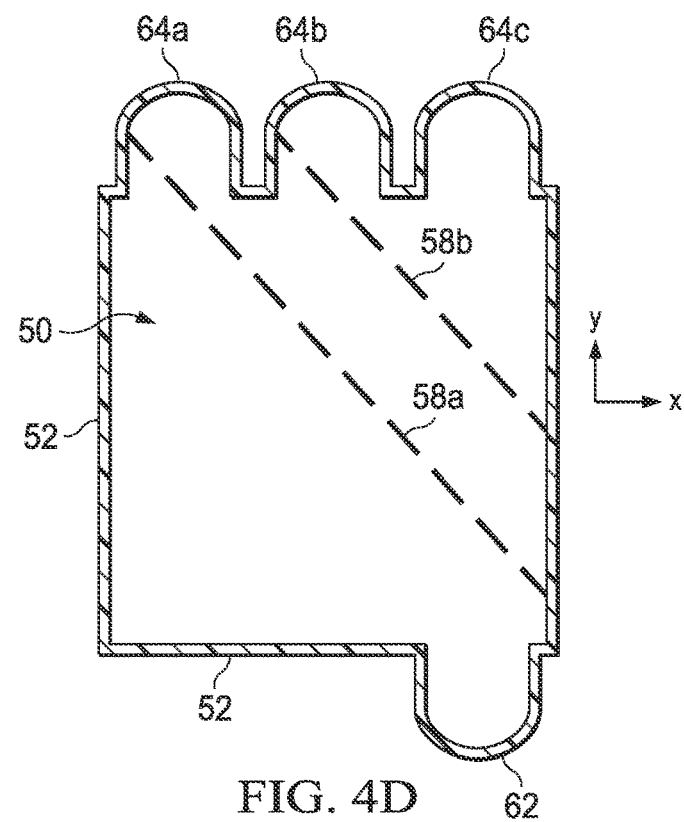
FIG. 4D is a top longitudinal cross-sectional schematic diagram of a flow-through magnetic separation/debeading module in a multiple zero-gradient configuration to create a multiple zero-gradient filter.
Figure 12:
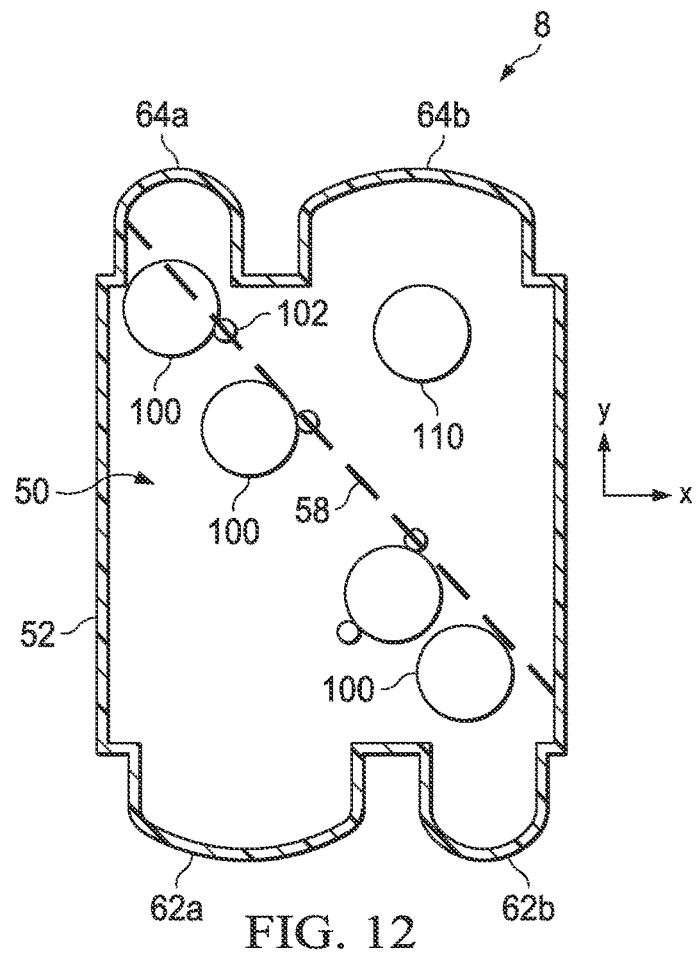
FIG. 12 is a diagram of the flow-through magnetic separation/debeading module of FIG. 4C with cells present during magnetic separation of paramagnetic particle-bound cells and unbound cells.

FIG. 12 shows cells moving through module 8 of FIG. 4C. Cells 100 with paramagnetic particles 102 follow zero gradient line 58 and are directed to magnetic outlet 64a. Unbound cells 110 are unaffected by zero gradient line 58 and flow to non-magnetic outlet 64b. Thus, zero gradient line 58 acts as a magnetic filter while allowing all cells to continue to move through chamber 50 without being pushed towards any wall 52. As illustrated non-magnetic inlet 62a is larger than magnetic inlet 62b and non-magnetic outlet 64b is larger than magnetic outlet 64a. If fluid flow in module 8 is laminar, fluid from non-magnetic inlet 62a crosses over to non-magnetic outlet 64b, preventing any unbound cells 110 from entering magnetic outlet 64*a*. This method may also be used with turbulent flow, but with less efficiency due to loss of unbound cells to the magnetic outlet 64*a*.

This flow-through separation process may remove at least 80%, at least 90%, at least 95%, or at least 99% of paramagnetic particle-bound cells 100 from the cell suspension prior to its entry into non-magnetic output module 10. Multiple passes of either the non-magnetic output or the magnetic output through flow-through magnetic separation/debeading module 8 may result in a paramagnetic particle-bound cell product with no more than 1% unbound cells 11 and containing at least 99% of the paramagnetic particle-bound cells 100 found in the cell suspension prior to the flow-through separation process, an unbound cell product with no more than 1% paramagnetic particle-bound cells 100 and containing at least 99% of the unbound cells 110 found in the cell suspension prior to the flow-through process, or both.

Flow-Through Zero Gradient Paramagnetic Particle Separation Process

Figure 13:
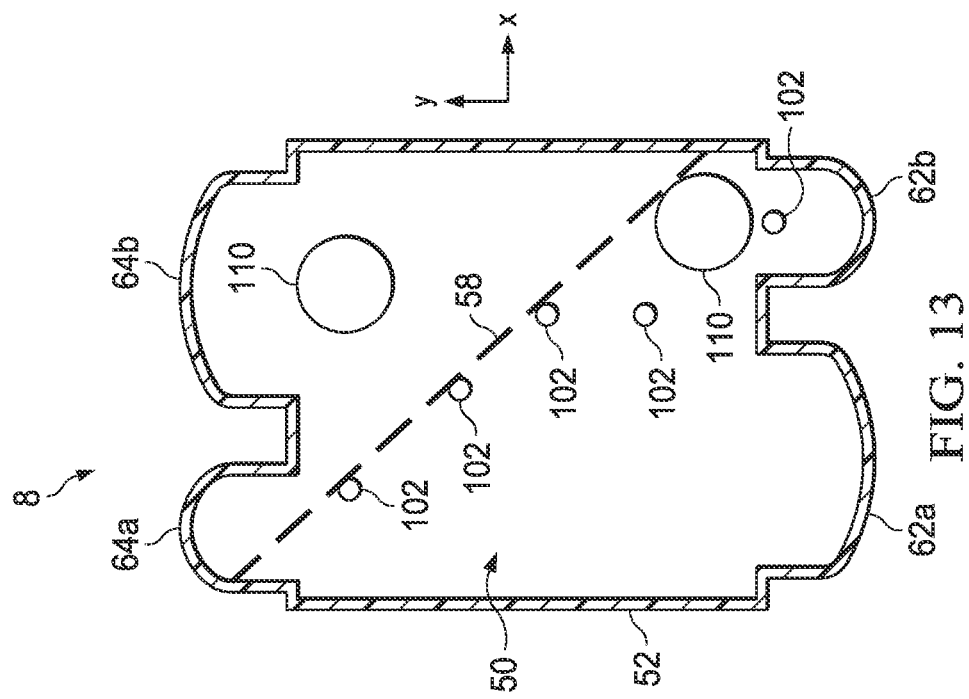
FIG. 13 is a diagram of the flow-through magnetic separation/debeading module of FIG. 4C with cells present during magnetic separation of paramagnetic particles from debeaded, unbound cells.

A flow-through paramagnetic particle separation process may also be conducted using flow-through magnetic separation/debeading module 8 in a configuration as shown in FIG. 4C. FIG. 13 shows debeaded, unbound cells 110 and paramagnetic particles 102 moving through module 8. Cells 110 were previously debeaded, for instance by spinning membrane debeading module 18, a non-spinning membrane debeading module, or the same or a separate module 8 in a debeading configuration. Alternatively, cells 110 may have already been in the presence of, but not bound to paramagnetic particles 102. Paramagnetic particles 102 follow zero gradient line 58 and are directed to magnetic outlet 64*a*. Debeaded, unbound cells 110 are unaffected by zero gradient line 58 and flow to non-magnetic outlet 64*b*. Thus, zero gradient line 58 acts as a magnetic filter while allowing cells 110 to continue to move through chamber 50 without being pushed towards any wall 52.

This flow-through paramagnetic particle separation process may remove at least 80%, at least 90%, at least 95%, or at least 99% of beads from the cell suspension.

This process, in conjunction with removing the paramagnetic particles, may remove an unwanted constituent of the cell suspension as well.

Although the cell separation process and the particle separation process are described separately above, they may both occur simultaneously in the same module or system. For example, a separation module will typically remove both paramagnetic particle-bound cells and free paramagnetic particles from the cell suspension.

Spinning Membrane Debeading Processes

Figure 14:
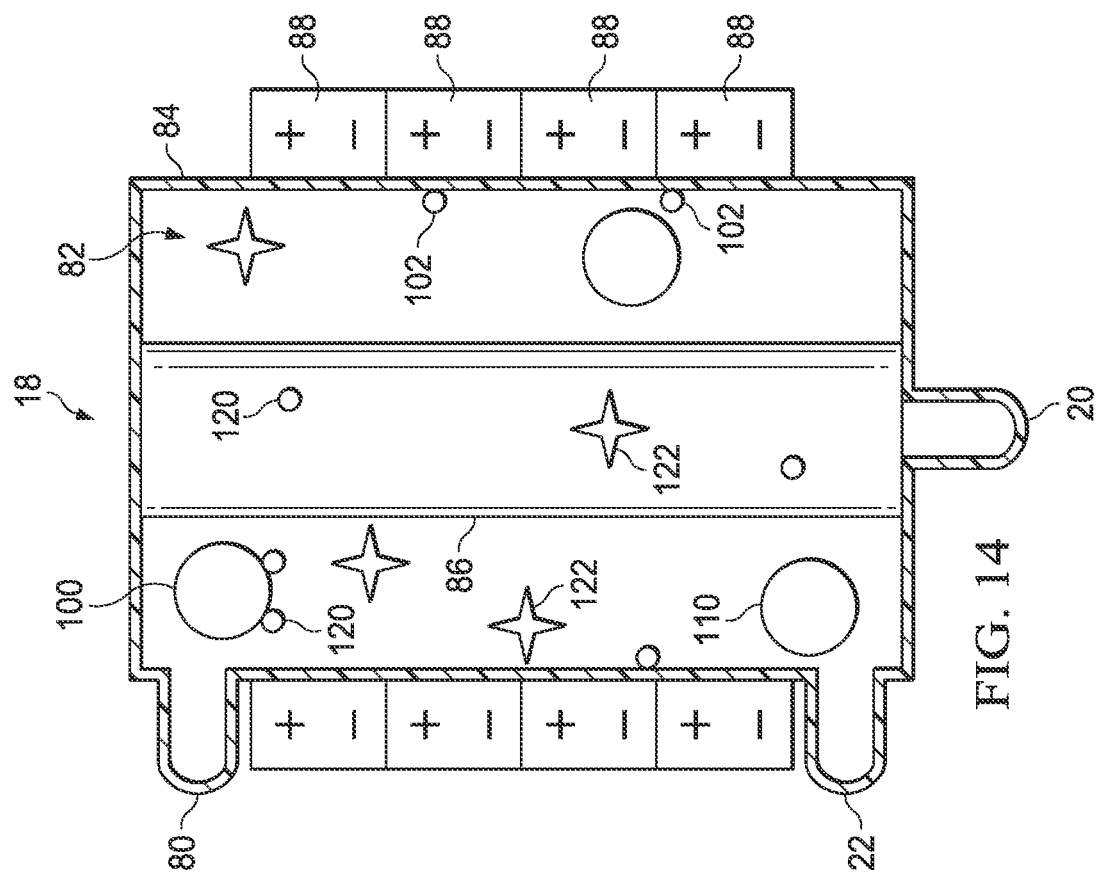
FIG. 14 is a diagram of the spinning membrane debeading module of FIG. 5 with cells present during debeading.

In a flow-through process using system 2 of FIG. 1F, separated paramagnetic particle-bound cells 100 are directed into spinning membrane module 18 as shown in FIG. 14 via sample inlet 80. Within debeading chamber 82, spinning membrane 86 generates recirculating Taylor-Couette flows in the cell suspension which cause fluidic forces in addition to the fluidic forces generated by flow through chamber 82 from inlet 80 to outlets 20 and 22. As a result, although paramagnetic particles 102 still experience a fluidic force and a magnetic force, the relationship of these forces and how they cause debeading is difficult to model. However, fluidic forces are affected by at least the size and spin rate of spinning membrane 80, the cell suspension flow rate through chamber 82, and the viscosity of the suspension fluid. Magnetic force is affected by the nature of paramagnetic particles 102, the nature of magnets 88, and the design of module 18, particularly distance between the cells 100 and magnets 88. Fluidic forces are typically not so high as to lyse the cells. The Taylor-Couette flows are sufficient to keep the cells away from and out of contact with wall 84 and spinning membrane 86.

Paramagnetic particles 102 that are removed from cells 100 migrate to wall 84, and particularly to zero gradient lines or bands along wall 84. Any non-paramagnetic particles 120 are also removed from cells 100 by fluidic forces alone. Non-paramagnetic particles 120 pass through pores in spinning membrane 86 and then exit chamber 82 via waste outlet module 20. Any chemical agent 122 added from optional reagent chamber 24 also passes through the pores in spinning membrane 86 and exits chamber 82 via waste outlet module 20. This limits exposure of cells 100 to chemical agent 120. Debeaded, unbound cells 110 exit chamber 82 via cell outlet module 22.

Paramagnetic particles 102 may be removed from wall 84 periodically, for instance by stopping cell suspension flow through chamber 82, moving magnets 88 to a position distant from wall 84, then flowing buffer through chamber 82.

Some paramagnetic particles 102 may also pass through spinning membrane 80 and be removed. If magnets 88 are absent or sufficiently distant from chamber 82, all paramagnetic particle removal may be accomplished by spinning membrane 80.

This flow-through debeading process may also remove at least 80%, at least 90%, at least 95%, or 99% of paramagnetic particles from the cells, at least 80%, at least 90%, at least 95%, or at least 99% of all non-paramagnetic particles from the cells, or both.

The spinning membrane may also be used to separate paramagnetic particles 102 from unbound cells 102.

Spinning membrane 86 may have a pore size small enough to exclude all cells in the cell suspension.

Spinning membrane module 18 may also be used to remove unwanted constituents from the cell suspension. These constituents may simply be filtered by spinning membrane 88, or they may interact with the coating of paramagnetic particles 102, non-paramagnetic particles 120, or both, and be removed with the particles. Debeading and unwanted constituent removal may occur separately or simultaneously.

Other Debeading and Paramagnetic Particle Separation Processes

System 2, due to it modular design, is also compatible with other debeading and paramagnetic particle separation processes. One need only insert an appropriate additional module 16. For instance, columns, including magnetic columns and physical separation methods are often used to debead cells and may be included as an additional module 16.

Other Incorporated Processes

System 2, due to its modular design, is compatible with other incorporated processes. These processes may occur in at least one additional module 16. For instance, a module may be used to wash cells. A module may also be used to concentrate cells. A module may be used to exchange the media in which cells are located. One module may be used for more than one of these steps.

Multiple-Module Flow-Through Process

System 2 as shown in FIG. 1G may be used in a multiple-module flow-through process. Optionally, buffer from buffer module 6*a* may be flowed through flow-through magnetic separation/debeading module 8*a* and optionally also one or more of modules 8*b*, 18*a*, and 18*b*. A cell suspension containing desirable, paramagnetic particle and non-paramagnetic particle-bound cells and undesirable unbound cells is flowed through module 8a, which is configured as shown in FIG. 4 for separation, but alternatively may be configured as shown in FIGS. 2A and 2B for separation. Unbound cells are directed to non-magnetic output module 10a as waste. Paramagnetic particle-bound cells are directed via magnetic output module 12a to flow-through magnetic separation/debeading module 8b. Module 8b is configured as shown in FIGS. 2A and 2B for debeading. Paramagnetic particle-bound cells are flowed through return loop 14a at least once prior to entering magnetic output module 12b as waste. Debeaded, unbound cells are sent via non-magnetic output module 10b to spinning membrane debeading module 18a. Any remaining paramagnetic particles and non-paramagnetic particles are removed, with non-paramagnetic particles flowing into waste output module 20a, while unbound paramagnetic particles remain in module 18 and unbound cells and cells with paramagnetic particles, non-paramagnetic particles, or both flow into cell output module 22a. Cell output module 22a leads to a second spinning membrane module 18b. A chemical agent able to facilitate removal of either the paramagnetic particle or the non-paramagnetic particle, or both, from the cells is added from reagent module 24. Non-paramagnetic particles and the chemical agent flow into waste module 20b. Paramagnetic particles remain in module 18. Unbound cells and cells with either paramagnetic particles, non-paramagnetic particles, or both flow into return loop 14b at least once prior to being sent to cell output module 22b as the final cell product of the flow-through process.

Clinical Applications

All of the processes herein may be conducted according to clinical good manufacturing practice (cGMP) standards.

The processes may be used for cell purification, enrichment, harvesting, washing, concentration or for cell media exchange, particularly during the collection of raw, starting materials (particularly cells) at the start of the manufacturing process, as well as during the manufacturing process for the selection or expansion of cells for cell therapy.

The cells may include any plurality of cells. The cells may be of the same cell type, or mixed cell types. In addition, the cells may be from one donor, such as an autologous donor or a single allogenic donor for cell therapy. The cells may be obtained from patients by, for example, leukapheresis or apheresis. The cells may include T cells, for example may include a population that has greater than 50% T cells, greater than 60% T cells, greater than 70% T cells, greater than 80% T cells, or 90% T cells.

Selection processes may be particularly useful in selecting cells prior to culture and expansion. For instance, paramagnetic particles coated with anti-CD3 and/or anti CD28 may be used to select T cells for expansion or for introduction of a nucleic acid encoding a chimeric antigen receptor (CAR) or other protein. Such a process is used to produce CTL019 T cells for treatment of acute lymphoblastic leukemia (ALL).

The debeading processes and modules disclosed herein may be particularly useful in the manufacture of cells for cell therapy, for example in purifying cells prior to, or after, culture and expansion. For instance, paramagnetic particles coated with anti-CD3 and/or anti CD28 antibodies may be used to selectively expand T cells, for example T cells that are, or will be, modified by introduction of a nucleic acid encoding a chimeric antigen receptor (CAR) or other protein, such that the CAR is expressed by the T cells. During the manufacture of such T cells, the debeading processes or modules may be used to separate T cells from the paramagnetic particles. Such a debeading process or module is used to produce, for example, CTL019 T cells for treatment of acute lymphoblastic leukemia (ALL).

In one such process, illustrated here by way of example, cells, for example, T cells, are collected from a donor (for example, a patient to be treated with an autologous chimeric antigen receptor T cell product) via apheresis (e.g., leukapheresis). Collected cells may then be optionally purified, for example, by an elutriation step. Paramagnetic particles, for example, anti-CD3/anti-CD28-coated paramagnetic particles, may then be added to the cell population, to expand the T cells. The process may also include a transduction step, wherein nucleic acid encoding one or more desired proteins, for example, a CAR, for example a CAR targeting CD19, is introduced into the cell. The nucleic acid may be introduced in a lentiviral vector. The cells, e.g., the lentivirally transduced cells, may then be expanded for a period of days, for example, 1, 2, 3, 4, 5, 6, 7, 8, 9, 10, or more days, for example in the presence of a suitable medium. After expansion, the debeading processes/modules disclosed herein may be used to separate the desired T cells from the paramagnetic particles. The process may include one or more debeading steps according to the processes of the present disclosure. The debeaded cells may then be formulated for administration to the patient. Examples of CAR T cells and their manufacture are further described, for example, in WO2012/079000, which is incorporated herein by reference in its entirety. The systems and methods of the present disclosure may be used for any cell separation/purification/debeading processes described in or associated with WO2012/079000.

The systems and methods herein may similarly benefit other cell therapy products by wasting fewer desirable cells, causing less cell trauma, and more reliably removing magnetic and any non-paramagnetic particles from cells with less or no exposure to chemical agents, as compared to conventional systems and methods.

EXAMPLE

The following example is provided for illustrative purposes only and is not intended to encompass the entire invention. Aspects of this example may be combined with other aspects of the invention described above.

In this example, T cells were expanded over a 9-day period in culture, then harvested and debeaded using a non flow-through debeading process according to prior procedures or a flow-through debeading process according to the present disclosure. The samples had between approximately 1e8 nucleated viable cells and approximately 3e10 nucleated viable cells. The paramagnetic particle to nucleated viable cell ratio was between approximately 3:1 and 1:3, with samples having lower total nucleated viable cells exhibiting higher paramagnetic particle to nucleated viable cell ratios. The paramagnetic particle to cell ratio was a significant factor in cell recovery. A higher paramagnetic particle to nucleated viable cell ratio increased the chances that a nucleated viable cell is bound to a paramagnetic particle and is lost during the paramagnetic particle removal process.

In the non flow-through debeading process, the sample was collected in a one liter platelet bag (Terumo Medical Corp., Somerset, N.J.) and statically placed on top of a flat-bed magnetic plate (DYNAMAG™ CTS™, Thermo Fisher Scientific, Waltham, Mass.) of 5 minutes at zero degrees, followed by one minute at a 30 degree inclination. Next, the liquid in the bag, which contained the non-magnetic fraction, was diverted from the bag to form the final product. The magnetic fraction remained inside the bag as waste.

In the flow-through debeading process, the sample was continuously flowed through a CSD400Y9 CRYOSTORE™ Conical Bag (OriGen Biomedical, Austin, Tex.) placed on top a flat-bed magnetic plate (DYNAMAG™ CTS™, Thermo Fisher Scientific, Waltham, Mass.). Due to continuous flow through the bag and over the magnet, the sample was dynamically debeaded, with paramagnetic particles being stripped off the viable nucleated cells as they moved through the bag. The liquid after passaging through the bag for some time formed the final product. The magnetic fraction remained inside the bag as waste. Few viable nucleated cells were trapped in the magnetic faction. This is in contrast to the non flow-through debeading process, which viable nucleated cells bound to paramagnetic particles were attracted to the magnet and lost in the waste.

Figure 15:
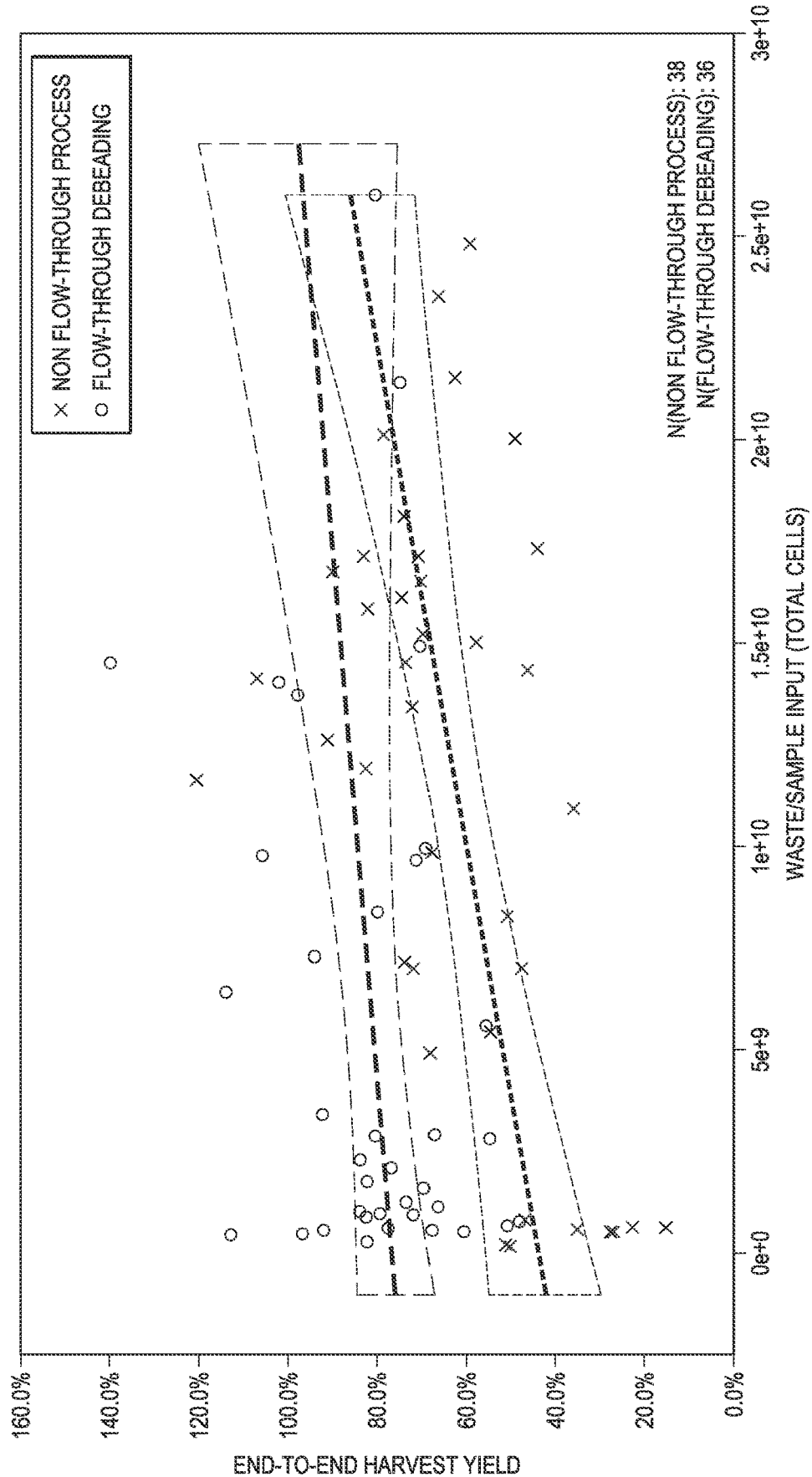
FIG. 15 is a graph of the harvest yields for a non flow-through debeading process and a flow-through debeading process as a function if input cell number.
Figure 16:
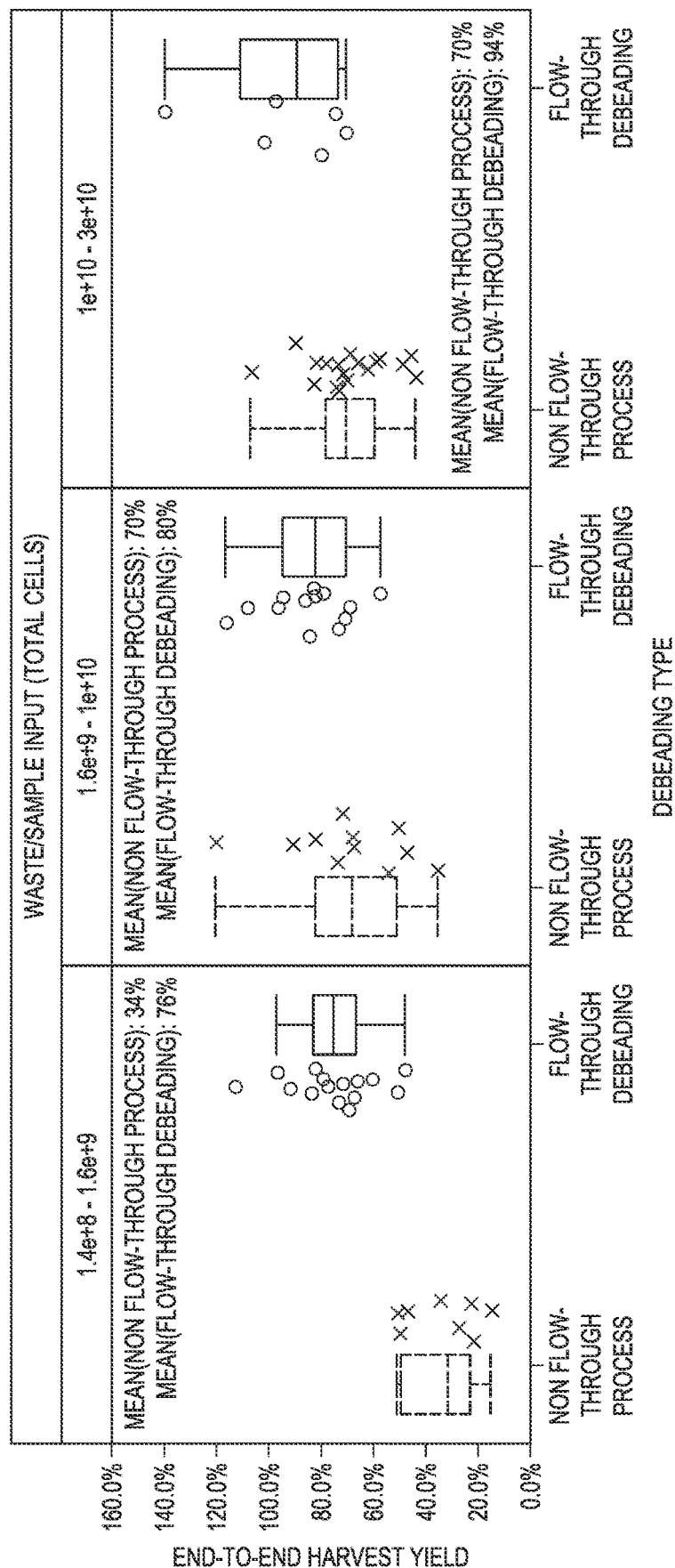
FIG. 16 is a binned graph of the harvest yields for a non flow-through debeading process and a flow-through debeading process as a function of input cell number.

Metadata analysis of thirty-eight non flow-through debeading process runs and thirty-six flow-through debeading process runs showed significant increases in recovery of viable nucleated cells when the flow-through debeading process was used. FIG. 15. The increase in viable nucleated cell recovery was particularly significant at lower numbers of cells in the sample (such as less than 1.6e9 total viable nucleated cells). At such total viable nucleated cell numbers, the flow-through debeading process exhibited a 76% average recovery as compared to only 34% average recovery for the non flow-through debeading process. FIG. 16. A 10-20% increase in recovery was also seen with higher numbers of cells in the sample.

This difference in recovery is due to the ability of the flow-through debeading process to dynamically remove paramagnetic particles from the viable nucleated cells, so that these cells are not lost even if they were initially bound to paramagnetic particles prior to harvest.

Although only exemplary embodiments of the disclosure are specifically described above, it will be appreciated that modifications and variations of these examples are possible without departing from the spirit and intended scope of the disclosure. For example, the magnetic modules and systems containing them may be arranged and used in a variety of configurations in addition to those described. In addition, the systems and methods may include additional components and steps not specifically described herein. For instance, methods may include priming, where a fluid is first introduced into a component to remove bubbles and reduce resistance to cell suspension or buffer movement. Furthermore, embodiments may include only a portion of the systems described herein for use with the methods described herein. For example, embodiments may relate to disposable modules, hoses, etc. usable within non-disposable equipment to form a complete system able to separate or debead cells to produce a cell product.

The invention claimed is:

1. A cell processing system comprising:
   a flow-through magnetic separation/debeading module, comprising:
      a flow chamber defined by a plurality of walls,
      an inlet arranged at a first end of the flow chamber for flowing a cell suspension comprising paramagnetic particle-bound cells and unbound cells into the flow chamber,
      an outlet arranged at a second end of the flow chamber opposite the first end of the flow chamber,
      a magnet assembly adjacent or proximate a wall of the flow chamber and configured to assert a magnetic force within the flow chamber,
      a plurality of fluid injection ports arranged along a wall of the plurality of walls of the flow chamber, the plurality of fluid injection ports being positioned between the first end and the second end of the flow chamber, and
      a membrane located above the plurality of fluid injection ports, wherein the membrane is configured to allow a fluid introduced through the plurality of injection ports to supply a force to any cells of the cell suspension stuck to the membrane sufficient to dislodge the cells from the membrane;
   wherein the magnetic separation/debeading module is configured to establish the magnetic force within the flow chamber and the flow of the cell suspension through the flow chamber to both separate the paramagnetic particle-bound cells from the unbound cells and to debead a portion of the paramagnetic particle-bound cells.

2. The cell processing system of claim 1, further comprising a spinning membrane debeading module positioned downstream from the at least one flow-through magnetic separation/debeading module.

3. The cell processing system of claim 1, wherein the magnet assembly comprises at least two permanent magnets housed on a movable platform.

4. The cell processing system of claim 3, wherein the movable platform is configured to move to adjust an amount of the magnetic force asserted within the flow chamber.

5. The cell processing system of claim 1, wherein the magnet assembly comprises an electromagnet.

6. The cell processing system of claim 1, wherein the walls of the flow chamber are flexible.

7. The cell processing system of claim 1, further comprising a return loop configured to return the separated unbound cells or the separated particle-bound cells back through the flow-through magnetic separation/debeading module.

8. The cell processing system of claim 7, further comprising at least one additional module.

9. The cell processing system of claim 8, wherein the at least one additional module comprises at least one physical separation module.

10. The cell processing system of claim 7, wherein the at least one additional module comprises at least one media exchange module.

11. The cell processing system of claim 7, wherein the at least one additional module comprises at least one cell concentration module.

12. The cell processing system of claim 7, wherein the at least one additional module comprises at least one cell washing module.

13. A method for processing paramagnetic particle-bound cells, comprising:
   flowing a cell suspension comprising paramagnetic particle-bound cells and unbound cells through a flow chamber of a flow-through magnetic separation/debeading module; and
   flowing fluid through a plurality of fluid injection ports arranged along the flow-through magnetic separation/debeading module, the plurality of fluid injection ports being positioned between a first end and a second end of the flow-through magnetic separation/debeading module, the fluid flowing through the plurality of fluid injection ports dislodging cells from a membrane positioned adjacent to the plurality of fluid injection ports, the dislodged cells passing further through the flow chamber;

wherein the magnetic separation/debeading module establishes a magnetic force within the flow chamber and a flow of the cell suspension through the flow chamber to both separate the paramagnetic particle-bound cells from the unbound cells and to debead a portion of the paramagnetic particle-bound cells.

14. The method of claim 13, further comprising:
flowing the separated paramagnetic particle-bound cells through the flow-through magnetic separation/debeading module again to debead the paramagnetic particle-bound cells using a return loop.

15. The method of claim 13, wherein the flow chamber comprises a plurality of walls, wherein the flow-through magnetic separation/debeading module further comprises
a magnet assembly comprising at least two magnets arranged proximate at least one wall of the plurality of walls of the flow chamber.

16. The method of claim 13, further comprising flowing the separated paramagnetic particle-bound cells through a spinning membrane debeading module.

17. The method of claim 13, further comprising flowing the separated unbound cells through the flow-through magnetic separation/debeading module again using a return loop to separate any paramagnetic particle-bound cells from particle-bound cells that were not separated from the unbound cells.

* * * * *